United States Patent
Ziegelaar et al.

(10) Patent No.: US 11,618,782 B2
(45) Date of Patent: Apr. 4, 2023

(54) METHODS AND AGENTS FOR THE TREATMENT OF OCULAR DISEASE

(71) Applicant: Line 6 Biotechnology, Inc., Seattle, WA (US)

(72) Inventors: Brian W. Ziegelaar, Brisbane (AU); Garry L. Redlich, Brisbane (AU)

(73) Assignee: Line 6 Biotechnology, Inc., Seattle, WA (US)

( * ) Notice: Subject to any disclaimer, the term of this patent is extended or adjusted under 35 U.S.C. 154(b) by 0 days.

(21) Appl. No.: 17/678,861

(22) Filed: Feb. 23, 2022

(65) Prior Publication Data

US 2022/0220194 A1 Jul. 14, 2022

Related U.S. Application Data

(63) Continuation of application No. PCT/AU2021/051173, filed on Oct. 7, 2021.

(51) Int. Cl.
*C07K 16/22* (2006.01)
*C07K 16/28* (2006.01)
*C07K 16/46* (2006.01)

(52) U.S. Cl.
CPC ............ *C07K 16/22* (2013.01); *C07K 16/468* (2013.01); *C07K 16/28* (2013.01); *C07K 2317/565* (2013.01); *C07K 2317/567* (2013.01)

(58) Field of Classification Search
None
See application file for complete search history.

(56) References Cited

U.S. PATENT DOCUMENTS

| | | | |
|---|---|---|---|
| 5,820,858 A | 10/1998 | Leturcq et al. | |
| 6,444,206 B1 | 9/2002 | Leturcq et al. | |
| 7,326,569 B2 | 2/2008 | Leturcq et al. | |
| 10,407,510 B2 * | 9/2019 | Kelley | A61K 39/39591 |
| 2006/0121574 A1 * | 6/2006 | Allison | C07K 16/00 536/23.53 |
| 2015/0126458 A1 * | 5/2015 | Hohman | A61K 9/0048 514/20.8 |
| 2016/0038589 A1 * | 2/2016 | Patel | C07K 16/22 424/134.1 |
| 2016/0319002 A1 * | 11/2016 | Bansal | A61P 27/02 |
| 2016/0340424 A1 * | 11/2016 | Senn | A61P 29/00 |

FOREIGN PATENT DOCUMENTS

| | | |
|---|---|---|
| KR | 1020190059164 A | 5/2019 |
| WO | WO 2002/42333 A1 | 5/2002 |
| WO | WO 2006/121871 A2 | 11/2006 |
| WO | WO 2009/002790 A2 | 12/2008 |
| WO | WO 2018/191786 A1 | 10/2018 |
| WO | WO 2022/073072 A1 | 4/2022 |

OTHER PUBLICATIONS

Lee et al., Ophthalmol Vis Sci, 59:715-721, 2018.*
Ishikawa et al., Experimental Eye Research, 142:19-25, 2016.*
International Search Report and Written Opinion of the International Searching Authority for International Application No. PCT/AU2021/051173, dated Nov. 11, 2021, 8 pages.
Adachi et al., "Inhibition by a CD14 monoclonal antibody of lipopolysaccharide binding to murine macrophages," J. Endotoxin Res., 1999, 5(3): 139-146.
Ahn et al., "Subretinal fibrosis after antivascular endothelial growth factor therapy in eyes with myopic choroidal neovascularization," Retina, 2016, 36(11): 2140-2149.
Alsalamah et al., "Recognizable Patterns of Submacular Fibrosis in Enhanced S-Cone Syndrome," Opthalmol Retina, 2021, 5(9): 918-927.
Axtelle et al., "IC14, a CD14 specific monoclonal antibody, is a potential treatment for patients with severe sepsis," J. Endotoxin Res., 2001, 7(4): 310-314.
Bazil et al., "Biochemical characterization of a soluble form of the 53-kDa monocyte surface antigen," Eur. J. Immunol., 1986, 16(12): 1583-1589.
Cetin et al., "Quantitative assessment of macular contraction and vitreoretinal interface alterations in diabetic macular edema treated with intravitreal anti-VEGF injections," Graefe's Archive for Clinical and Experimental Ophthalmology, Jun. 2018, 256: 1801-1806.
Cogan et al., "Topical Delivery of Anti-VEGF Drugs to the Ocular Posterior Segment Using Cell-Penetrating Peptides," Investigative Opthalmology & Visual Science, May 2017, 58(5): 2578-2590.
Daniel et al., "Risk of Scar in the Comparison of Age-related Macular Degeneration Treatments Trials," Opthalmology, Mar. 2014, 121(3): 656-666.
Daniel et al., "Development and Course of Scars in the Comparison of Age-related Macular Degenerations Treatments Trials (CATT)," Opthalmology, Jul. 2018, 125(7): 1037-1046.
Droho et al., "Monocyte-Derived Macrophages Are Necessary for Beta-Adrenergic Receptor-Driven Choroidal Neovascularization Inhibition," Invest Ophthalmol Vis Sci, Dec. 2019, 60(15): 5059-5069.
Enriquez et al., "Update on Anti-Vascular Endothelial Growth Factor Safety for Retinopathy of Prematurity," Asia-Pacific Journal of Opthalmology, Aug. 2020, 9(4): 358-368.
Funk et al., "Angiogenic and Inflammatory Markers in the Intraocular Fluid of Eyes With Diabetic Macular Edema and Influence of Therapy With Bevacizumab," Retina, 2010, 30(9): 1412-1419.
Gao et al., "A serum metabolomics study of patients with nAMD in response to anti-VEGF therapy," Scientific Reports, 2020, 10:1341, 10 pages.
Golzarri et al., "Risk factors for subretinal fibrosis in patients with Vogt Koyanagi Harada syndrome," Ocul Immunol Inflamm Oct. 2020, 6:1-5.

(Continued)

*Primary Examiner* — Marianne P Allen
(74) *Attorney, Agent, or Firm* — Cooley LLP

(57) ABSTRACT

This disclosure relates generally to methods and agents for treating an ocular disease or disorder. More particularly, the present disclosure relates to the use of CD14 antagonist antibodies for treating an ocular disease or disorder.

16 Claims, 12 Drawing Sheets
Specification includes a Sequence Listing.

(56) References Cited

OTHER PUBLICATIONS

Hu et al., "Recurrence of Retinopathy of Prematurity in Zone II Stage 3+ after Ranibizumab Treatment: A Retrospective Study," J Ophthalmol, 2017, Article ID 5078565, pp. 1-5.

Idrees et al., "Proliferative Vitreoretinopathy: A Review," Int. Opthalmol Clin., 2019, 59(1): 221-240.

Juan et al., "Identification of a Lipopolysaccharide Binding Domain in CD14 between Amino Acids 57 and 64," J. Biol. Chem., Mar. 1995, 270(10): 5219-5224.

Juan et al., "Identification of a Domain in Soluble CD14 Essential for Lipopolysaccharide (LPS) Signaling but Not LPS Binding," J. Biol. Chem., Jul. 1995, 270(29): 17237-17242.

Khojasteh et al., "Autosomal Recessive Bestrophinopathy: Clinical and Genetic Characteristics of Twenty-Four Cases," J. Opthalmol, Apr. 2021, Article ID 6674290, 11 pages.

Lau et al., "Chimeric Anti-CD 14 IGG2/4 Hybrid Antibodies for Therapeutic Intervention in Pig and Human Models of Inflammation," The Journal of Immunology, Sep. 2013, 191: 4769-4777.

Leturcq et al., "Antibodies against CD14 protect primates from endotoxininduced shock." J. Clin. Invest, Oct. 1996, 98(7): 1533-1538.

Li et al., "Changes in vitreous VEGF, bFGF and fibrosis in proliferative diabetic retinopathy after intravitreal bevacizumab," Int J Ophthalmol, Dec. 2015, 8(6): 1202-1206.

Mandal et al., "Ocular delivery of proteins and peptides: Challenges and novel formulation approaches," Advanced Drug Delivery Reviews, Jan. 2018, vol. 126: 67-95.

Marano et al., "Hereditary retinal dystrophies and choroidal neovascularization," Graefe's Arch Cln Exp Opthalmol, 2000, 238: 760-764.

Murakami et al., "Innate immune response in retinal homeostasis and inflammatory disorders." Progress in Retinal and Eye Research, 2020, 74: 100778.

Osaadon, "A review of anti-VEGF agents for proliferative diabetic retinopathy," Eye (Lond), Feb. 2014, 28(5): 510-520.

ROY et al., "Retinal Fibrosis in Diabetic Retinopathy," Experimental Eye Research, Jan. 2016, 142: 71-75.

Schlunck et al., "Conjunctival fibrosis following filtering glaucoma surgery," Exp. Eye Res., 2016, 142: 76-82.

Sen et al., "Coats disease: An overview of classification, management and outcomes," Indian J. Opthalmol, 2019, 67(6): 763-771.

Shen et al., "Construction and Expression of a Novel Anti-CD 14 Human-Mouse Chimeric Antibody Hm2F9," DNA Cel Biol., 2014, 33(9): 599-604.

Tang et al., "Construction and Expression of Single-Chain Antibody Derived from a New Clone of Monoclonal Antibody Against Human CD14 in CHO Cells," Immunopharmacol Immunotoxicol, 2007, 29: 375-386.

Tarib et al., "An Atypical Idiopathic Retinal Vasculitis, Aneurysms and Neuroretinitis IRVAN: Case Report," J Clin Exp Ophthal, Feb. 2020, vol. 11, Issue 1, No. 1000824, 4 pages.

Tasaka et al., "Effect of CD14 Blockade on Endotoxin-Induced Acute Lung Injury in Mice," Am. J. Respir. Cell. Mol. Biol., 2003, 29(2): 252-258.

Tong et al., "Outcomes and prognostic factors for aggressive posterior retinopathy of prematurity following initial treatment with intravitreal ranibizumab," BMC Ophthalmology, Jun. 2018, 18:150, 9 pages.

Tsutsumi et al., "The critical role of ocular-infiltrating macrophages in the development of choroidal neovascularization," J Leukoc Biol, Jul. 2003, 74(1): 25-32.

van Voorhis et al., "Specific Antimononuclear Phagocyte Monoclonal Antibodies," J. Exp. Med., Jul. 1983, 158: 126-145.

Xiao et al., "Risk factors for subretinal fibrosis after anti-VEGF treatment of myopic choroidal neovascularisation," Br J Ophthalmol, 2020.

Zhavoronkov et al., "Pro-fibrotic pathway activation in trabecular meshwork and lamina cribrosa is the main driving force of glaucoma," Cell Cycle, 2016, 15(12): 1643-1652.

Zhu et al., "Anti-vascular endothelial growth factor for choroidal neovascularisation in people with pathological myopia (Review)," Cochrane Database of Systematic Reviews, 2016, Issue 12, Art No. CD011160, 56 pages.

\* cited by examiner

A.

B.

A.

B.

C.

D.

E.

F.

A.

B.

A.

B.

C.

SEQUENCE LISTING

<160> NUMBER OF SEQ ID NOS: 33

<210> SEQ ID NO 1
<211> LENGTH: 106
<212> TYPE: PRT
<213> ORGANISM: Artificial Sequence
<220> FEATURE:
<223> OTHER INFORMATION: VL domain

<400> SEQUENCE: 1

Gln Ser Pro Ala Ser Leu Ala Val Ser Leu Gly Gln Arg Ala Thr Ile
1               5                   10                  15

Ser Cys Arg Ala Ser Glu Ser Val Asp Ser Phe Gly Asn Ser Phe Met
            20                  25                  30

His Trp Tyr Gln Gln Lys Ala Gly Gln Pro Pro Lys Ser Ser Ile Tyr
        35                  40                  45

Arg Ala Ala Asn Leu Glu Ser Gly Ile Pro Ala Arg Phe Ser Gly Ser
    50                  55                  60

Gly Ser Arg Thr Asp Phe Thr Leu Thr Ile Asn Pro Val Glu Ala Asp
65                  70                  75                  80

Asp Val Ala Thr Tyr Phe Cys Gln Gln Ser Tyr Glu Asp Pro Trp Thr
                85                  90                  95

Phe Gly Gly Gly Thr Lys Leu Gly Asn Gln
            100                 105

<210> SEQ ID NO 2
<211> LENGTH: 105
<212> TYPE: PRT
<213> ORGANISM: Artificial Sequence
<220> FEATURE:
<223> OTHER INFORMATION: VH domain

<400> SEQUENCE: 2

Leu Val Lys Pro Gly Gly Ser Leu Lys Leu Ser Cys Val Ala Ser Gly
1               5                   10                  15

Phe Thr Phe Ser Ser Tyr Ala Met Ser Trp Val Arg Gln Thr Pro Glu
            20                  25                  30

Lys Arg Leu Glu Trp Val Ala Ser Ile Ser Ser Gly Gly Thr Thr Tyr
        35                  40                  45

Tyr Pro Asp Asn Val Lys Gly Arg Phe Thr Ile Ser Arg Asp Asn Ala
    50                  55                  60

Arg Asn Ile Leu Tyr Leu Gln Met Ser Ser Leu Arg Ser Glu Asp Thr
65                  70                  75                  80

Ala Met Tyr Tyr Cys Ala Arg Gly Tyr Tyr Asp Tyr His Tyr Trp Gly
                85                  90                  95

Gln Gly Thr Thr Leu Thr Val Ser Ser
            100                 105

<210> SEQ ID NO 3
<211> LENGTH: 106
<212> TYPE: PRT
<213> ORGANISM: Artificial Sequence
<220> FEATURE:
<223> OTHER INFORMATION: VL domain

<400> SEQUENCE: 3

Gln Ser Pro Ala Ser Leu Ala Val Ser Leu Gly Gln Arg Ala Thr Ile
1               5                   10                  15

Ser Cys Arg Ala Ser Glu Ser Val Asp Ser Tyr Val Asn Ser Phe Leu
            20                  25                  30

```
His Trp Tyr Gln Gln Lys Pro Gly Gln Pro Lys Leu Leu Ile Tyr
        35                  40                  45

Arg Ala Ser Asn Leu Gln Ser Gly Ile Pro Ala Arg Phe Ser Gly Ser
 50                  55                  60

Gly Ser Arg Thr Asp Phe Thr Leu Thr Ile Asn Pro Val Glu Ala Asp
 65                  70                  75                  80

Asp Val Ala Thr Tyr Cys Cys Gln Gln Ser Asn Glu Asp Pro Thr Thr
                 85                  90                  95

Phe Gly Gly Gly Thr Lys Leu Glu Ile Lys
             100                 105

<210> SEQ ID NO 4
<211> LENGTH: 112
<212> TYPE: PRT
<213> ORGANISM: Artificial Sequence
<220> FEATURE:
<223> OTHER INFORMATION: VH domain

<400> SEQUENCE: 4

Leu Gln Gln Ser Gly Pro Gly Leu Val Lys Pro Ser Gln Ser Leu Ser
1                5                  10                  15

Leu Thr Cys Thr Val Thr Gly Tyr Ser Ile Thr Ser Asp Ser Ala Trp
                 20                  25                  30

Asn Trp Ile Arg Gln Phe Pro Gly Asn Arg Leu Glu Trp Met Gly Tyr
             35                  40                  45

Ile Ser Tyr Ser Gly Ser Thr Ser Tyr Asn Pro Ser Leu Lys Ser Arg
 50                  55                  60

Ile Ser Ile Thr Arg Asp Thr Ser Lys Asn Gln Phe Phe Leu Gln Leu
65                  70                  75                  80

Asn Ser Val Thr Thr Glu Asp Thr Ala Thr Tyr Tyr Cys Val Arg Gly
                 85                  90                  95

Leu Arg Phe Ala Tyr Trp Gly Gln Gly Thr Leu Val Thr Val Ser Ala
             100                 105                 110

<210> SEQ ID NO 5
<211> LENGTH: 101
<212> TYPE: PRT
<213> ORGANISM: Artificial Sequence
<220> FEATURE:
<223> OTHER INFORMATION: VL domain

<400> SEQUENCE: 5

Gln Thr Pro Ser Ser Leu Ser Ala Ser Leu Gly Asp Arg Val Thr Ile
1                5                  10                  15

Ser Cys Arg Ala Ser Gln Asp Ile Lys Asn Tyr Leu Asn Trp Tyr Gln
                 20                  25                  30

Gln Pro Gly Gly Thr Val Lys Val Leu Ile Tyr Tyr Thr Ser Arg Leu
             35                  40                  45

His Ser Gly Val Pro Ser Arg Phe Ser Gly Ser Gly Ser Gly Thr Asp
 50                  55                  60

Tyr Ser Leu Thr Ile Ser Asn Leu Glu Gln Glu Asp Phe Ala Thr Tyr
65                  70                  75                  80

Phe Cys Gln Arg Gly Asp Thr Leu Pro Trp Thr Phe Gly Gly Gly Thr
                 85                  90                  95

Lys Leu Glu Ile Lys
             100
```

-continued

```
<210> SEQ ID NO 6
<211> LENGTH: 116
<212> TYPE: PRT
<213> ORGANISM: Artificial Sequence
<220> FEATURE:
<223> OTHER INFORMATION: VH domain

<400> SEQUENCE: 6

Leu Glu Ser Gly Pro Gly Leu Val Ala Pro Ser Gln Ser Leu Ser Ile
1               5                   10                  15

Thr Cys Thr Val Ser Gly Phe Ser Leu Thr Asn Tyr Asp Ile Ser Trp
            20                  25                  30

Ile Arg Gln Pro Pro Gly Lys Gly Leu Glu Trp Leu Gly Val Ile Trp
        35                  40                  45

Thr Ser Gly Gly Thr Asn Tyr Asn Ser Ala Phe Met Ser Arg Leu Ser
    50                  55                  60

Ile Thr Lys Asp Asn Ser Glu Ser Gln Val Phe Leu Lys Met Asn Gly
65                  70                  75                  80

Leu Gln Thr Asp Asp Thr Gly Ile Tyr Tyr Cys Val Arg Gly Asp Gly
                85                  90                  95

Asn Phe Tyr Leu Tyr Asn Phe Asp Tyr Trp Gly Gln Gly Thr Thr Leu
            100                 105                 110

Thr Val Ser Ser
        115

<210> SEQ ID NO 7
<211> LENGTH: 15
<212> TYPE: PRT
<213> ORGANISM: Artificial Sequence
<220> FEATURE:
<223> OTHER INFORMATION: L-CDR1

<400> SEQUENCE: 7

Arg Ala Ser Glu Ser Val Asp Ser Phe Gly Asn Ser Phe Met His
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: L-CDR2

<400> SEQUENCE: 8

Arg Ala Ala Asn Leu Glu Ser
1               5

<210> SEQ ID NO 9
<211> LENGTH: 9
<212> TYPE: PRT
<213> ORGANISM: Artificial Sequence
<220> FEATURE:
<223> OTHER INFORMATION: L-CDR3

<400> SEQUENCE: 9

Gln Gln Ser Tyr Glu Asp Pro Trp Thr
1               5

<210> SEQ ID NO 10
<211> LENGTH: 5
<212> TYPE: PRT
<213> ORGANISM: Artificial Sequence
<220> FEATURE:
<223> OTHER INFORMATION: H-CDR1
```

```
<400> SEQUENCE: 10

Ser Tyr Ala Met Ser
1               5

<210> SEQ ID NO 11
<211> LENGTH: 16
<212> TYPE: PRT
<213> ORGANISM: Artificial Sequence
<220> FEATURE:
<223> OTHER INFORMATION: H-CDR2

<400> SEQUENCE: 11

Ser Ile Ser Ser Gly Gly Thr Thr Tyr Tyr Pro Asp Asn Val Lys Gly
1               5                   10                  15

<210> SEQ ID NO 12
<211> LENGTH: 7
<212> TYPE: PRT
<213> ORGANISM: Artificial Sequence
<220> FEATURE:
<223> OTHER INFORMATION: H-CDR3

<400> SEQUENCE: 12

Gly Tyr Tyr Asp Tyr His Tyr
1               5

<210> SEQ ID NO 13
<211> LENGTH: 15
<212> TYPE: PRT
<213> ORGANISM: Artificial Sequence
<220> FEATURE:
<223> OTHER INFORMATION: L-CDR1

<400> SEQUENCE: 13

Arg Ala Ser Glu Ser Val Asp Ser Tyr Val Asn Ser Phe Leu His
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: L-CDR2

<400> SEQUENCE: 14

Arg Ala Ser Asn Leu Gln Ser
1               5

<210> SEQ ID NO 15
<211> LENGTH: 9
<212> TYPE: PRT
<213> ORGANISM: Artificial Sequence
<220> FEATURE:
<223> OTHER INFORMATION: L-CDR3

<400> SEQUENCE: 15

Gln Gln Ser Asn Glu Asp Pro Thr Thr
1               5

<210> SEQ ID NO 16
<211> LENGTH: 6
<212> TYPE: PRT
<213> ORGANISM: Artificial Sequence
<220> FEATURE:
<223> OTHER INFORMATION: H-CDR1
```

```
<400> SEQUENCE: 16

Ser Asp Ser Ala Trp Asn
1               5

<210> SEQ ID NO 17
<211> LENGTH: 16
<212> TYPE: PRT
<213> ORGANISM: Artificial Sequence
<220> FEATURE:
<223> OTHER INFORMATION: H-CDR2

<400> SEQUENCE: 17

Tyr Ile Ser Tyr Ser Gly Ser Thr Ser Tyr Asn Pro Ser Leu Lys Ser
1               5                   10                  15

<210> SEQ ID NO 18
<211> LENGTH: 6
<212> TYPE: PRT
<213> ORGANISM: Artificial Sequence
<220> FEATURE:
<223> OTHER INFORMATION: H-CDR3

<400> SEQUENCE: 18

Gly Leu Arg Phe Ala Tyr
1               5

<210> SEQ ID NO 19
<211> LENGTH: 11
<212> TYPE: PRT
<213> ORGANISM: Artificial Sequence
<220> FEATURE:
<223> OTHER INFORMATION: L-CDR1

<400> SEQUENCE: 19

Arg Ala Ser Gln Asp Ile Lys Asn Tyr Leu Asn
1               5                   10

<210> SEQ ID NO 20
<211> LENGTH: 7
<212> TYPE: PRT
<213> ORGANISM: Artificial Sequence
<220> FEATURE:
<223> OTHER INFORMATION: L-CDR2

<400> SEQUENCE: 20

Tyr Thr Ser Arg Leu His Ser
1               5

<210> SEQ ID NO 21
<211> LENGTH: 9
<212> TYPE: PRT
<213> ORGANISM: Artificial Sequence
<220> FEATURE:
<223> OTHER INFORMATION: L-CDR3

<400> SEQUENCE: 21

Gln Arg Gly Asp Thr Leu Pro Trp Thr
1               5

<210> SEQ ID NO 22
<211> LENGTH: 5
<212> TYPE: PRT
<213> ORGANISM: Artificial Sequence
<220> FEATURE:
<223> OTHER INFORMATION: H-CDR1

<400> SEQUENCE: 22
```

```
Asn Tyr Asp Ile Ser
1               5

<210> SEQ ID NO 23
<211> LENGTH: 16
<212> TYPE: PRT
<213> ORGANISM: Artificial Sequence
<220> FEATURE:
<223> OTHER INFORMATION: H-CDR2

<400> SEQUENCE: 23

Val Ile Trp Thr Ser Gly Gly Thr Asn Tyr Asn Ser Ala Phe Met Ser
1               5                   10                  15

<210> SEQ ID NO 24
<211> LENGTH: 12
<212> TYPE: PRT
<213> ORGANISM: Artificial Sequence
<220> FEATURE:
<223> OTHER INFORMATION: H-CDR3

<400> SEQUENCE: 24

Gly Asp Gly Asn Phe Tyr Leu Tyr Asn Phe Asp Tyr
1               5                   10

<210> SEQ ID NO 25
<211> LENGTH: 106
<212> TYPE: PRT
<213> ORGANISM: Artificial Sequence
<220> FEATURE:
<223> OTHER INFORMATION: VL domain

<400> SEQUENCE: 25

Gln Ser Pro Ala Ser Leu Ala Val Ser Leu Gly Gln Arg Ala Thr Ile
1               5                   10                  15

Ser Cys Arg Ala Ser Glu Ser Val Asp Ser Tyr Val Asn Ser Phe Leu
            20                  25                  30

His Trp Tyr Gln Gln Lys Pro Gly Gln Pro Pro Lys Leu Leu Ile Tyr
        35                  40                  45

Arg Ala Ser Asn Leu Gln Ser Gly Ile Pro Ala Arg Phe Ser Gly Ser
    50                  55                  60

Gly Ser Arg Thr Asp Phe Thr Leu Thr Ile Asn Pro Val Glu Ala Asp
65                  70                  75                  80

Asp Val Ala Thr Tyr Tyr Cys Gln Gln Ser Asn Glu Asp Pro Tyr Thr
                85                  90                  95

Phe Gly Gly Gly Thr Lys Leu Glu Ile Lys
            100                 105

<210> SEQ ID NO 26
<211> LENGTH: 112
<212> TYPE: PRT
<213> ORGANISM: Artificial Sequence
<220> FEATURE:
<223> OTHER INFORMATION: VH domain

<400> SEQUENCE: 26

Leu Gln Gln Ser Gly Pro Gly Leu Val Lys Pro Ser Gln Ser Leu Ser
1               5                   10                  15

Leu Thr Cys Thr Val Thr Gly Tyr Ser Ile Thr Ser Asp Ser Ala Trp
            20                  25                  30

Asn Trp Ile Arg Gln Phe Pro Gly Asn Arg Leu Glu Trp Met Gly Tyr
        35                  40                  45
```

```
Ile Ser Tyr Ser Gly Ser Thr Ser Tyr Asn Pro Ser Leu Lys Ser Arg
    50                  55                  60

Ile Ser Ile Thr Arg Asp Thr Ser Lys Asn Gln Phe Phe Leu Gln Leu
65                  70                  75                  80

Asn Ser Val Thr Thr Glu Asp Thr Ala Thr Tyr Tyr Cys Val Arg Gly
                85                  90                  95

Leu Arg Phe Ala Tyr Trp Gly Gln Gly Thr Leu Val Thr Val Ser Ser
            100                 105                 110
```

<210> SEQ ID NO 27
<211> LENGTH: 9
<212> TYPE: PRT
<213> ORGANISM: Artificial Sequence
<220> FEATURE:
<223> OTHER INFORMATION: L-CDR3

<400> SEQUENCE: 27

```
Gln Gln Ser Asn Glu Asp Pro Tyr Thr
1               5
```

<210> SEQ ID NO 28
<211> LENGTH: 213
<212> TYPE: PRT
<213> ORGANISM: Artificial Sequence
<220> FEATURE:
<223> OTHER INFORMATION: light chain

<400> SEQUENCE: 28

```
Gln Ser Pro Ala Ser Leu Ala Val Ser Leu Gly Gln Arg Ala Thr Ile
1               5                   10                  15

Ser Cys Arg Ala Ser Glu Ser Val Asp Ser Tyr Val Asn Ser Phe Leu
                20                  25                  30

His Trp Tyr Gln Gln Lys Pro Gly Gln Pro Pro Lys Leu Leu Ile Tyr
            35                  40                  45

Arg Ala Ser Asn Leu Gln Ser Gly Ile Pro Ala Arg Phe Ser Gly Ser
        50                  55                  60

Gly Ser Arg Thr Asp Phe Thr Leu Thr Ile Asn Pro Val Glu Ala Asp
65                  70                  75                  80

Asp Val Ala Thr Tyr Tyr Cys Gln Gln Ser Asn Glu Asp Pro Tyr Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

```
<210> SEQ ID NO 29
<211> LENGTH: 439
<212> TYPE: PRT
<213> ORGANISM: Artificial Sequence
<220> FEATURE:
<223> OTHER INFORMATION: heavy chain

<400> SEQUENCE: 29

Leu Gln Gln Ser Gly Pro Gly Leu Val Lys Pro Ser Gln Ser Leu Ser
1               5                   10                  15

Leu Thr Cys Thr Val Thr Gly Tyr Ser Ile Thr Ser Asp Ser Ala Trp
            20                  25                  30

Asn Trp Ile Arg Gln Phe Pro Gly Asn Arg Leu Glu Trp Met Gly Tyr
        35                  40                  45

Ile Ser Tyr Ser Gly Ser Thr Ser Tyr Asn Pro Ser Leu Lys Ser Arg
50                  55                  60

Ile Ser Ile Thr Arg Asp Thr Ser Lys Asn Gln Phe Phe Leu Gln Leu
65                  70                  75                  80

Asn Ser Val Thr Thr Glu Asp Thr Ala Thr Tyr Tyr Cys Val Arg Gly
                85                  90                  95

Leu Arg Phe Ala Tyr Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Ser Cys Pro Ala Pro
210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Tyr Arg Val Val Ser Val Leu Thr Val Leu His Gln Asp
290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
```

```
                370                 375                 380
Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
                420                 425                 430

Leu Ser Leu Ser Leu Gly Lys
            435
```

<210> SEQ ID NO 30
<211> LENGTH: 111
<212> TYPE: PRT
<213> ORGANISM: Artificial Sequence
<220> FEATURE:
<223> OTHER INFORMATION: VL domain

<400> SEQUENCE: 30

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Val Asn Ser Phe Leu His Trp Tyr Gln Gln Lys Pro Gly Gln Pro Pro
        35                  40                  45

Lys Leu Leu Ile Tyr Arg Ala Ser Asn Leu Gln Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110
```

<210> SEQ ID NO 31
<211> LENGTH: 115
<212> TYPE: PRT
<213> ORGANISM: Artificial Sequence
<220> FEATURE:
<223> OTHER INFORMATION: VH domain

<400> SEQUENCE: 31

```
Asp Val Gln Leu Gln Gln Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Ser Ala Trp Asn Trp Ile Arg Gln Phe Pro Gly Asn Arg Leu Glu Trp
        35                  40                  45

Met Gly Tyr Ile Ser Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Val Arg Gly Leu Arg Phe Ala Tyr Trp Gly Gln Gly Thr Leu Val Thr
            100                 105                 110

Val Ser Ser
        115
```

```
<210> SEQ ID NO 32
<211> LENGTH: 218
<212> TYPE: PRT
<213> ORGANISM: Artificial Sequence
<220> FEATURE:
<223> OTHER INFORMATION: light chain

<400> SEQUENCE: 32

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Val Asn Ser Phe Leu His Trp Tyr Gln Gln Lys Pro Gly Gln Pro Pro
        35                  40                  45

Lys Leu Leu Ile Tyr Arg Ala Ser Asn Leu Gln Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 33
<211> LENGTH: 442
<212> TYPE: PRT
<213> ORGANISM: Artificial Sequence
<220> FEATURE:
<223> OTHER INFORMATION: heavy chain

<400> SEQUENCE: 33

Asp Val Gln Leu Gln Gln Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Ser Ala Trp Asn Trp Ile Arg Gln Phe Pro Gly Asn Arg Leu Glu Trp
        35                  40                  45

Met Gly Tyr Ile Ser Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95
```

```
Val Arg Gly Leu Arg Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Cys Ser Arg Ser Thr Ser Glu Ser Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
            195                 200                 205

Val Asp Lys Arg Val Glu Ser Lys Tyr Gly Pro Pro Cys Pro Ser Cys
            210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
            275                 280                 285

Glu Gln Phe Asn Ser Thr Tyr Arg Val Val Ser Val Leu Thr Val Leu
            290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
            370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
            435                 440
```

METHODS AND AGENTS FOR THE TREATMENT OF OCULAR DISEASE

CROSS REFERENCE TO RELATED APPLICATIONS

This application is continuation of International Patent Application PCT/AU2021/051173 filed Oct. 7, 2021, which claims priority to Australian Provisional Application No. 2020903624 entitled "Methods and agents for the treatment of ocular disease" filed 7 Oct. 2020, the contents of which are herein incorporated by reference in its entirety for all purposes.

INCORPORATION BY REFERENCE OF SEQUENCE LISTING

The contents of the text file submitted electronically herewith are incorporated herein by reference in their entirety: A computer readable format copy of the Sequence Listing (filename: LBTI_001_01US_SubSeqList.txt, date created: Mar. 21, 2022, file size 25,910 bytes).

FIELD OF THE INVENTION

This disclosure relates generally to methods and agents for treating an ocular disease or disorder. More particularly, the present disclosure relates to the use of CD14 antagonist antibodies for treating an ocular disease or disorder.

BACKGROUND OF THE INVENTION

Ocular diseases cause vision impairment and blindness in millions of people worldwide, significantly affecting sufferers' quality of life. The diseases are complex and have differing and wide-ranging causes, and only limited therapeutic and management options.

Age-related macular degeneration (AMD) is the leading cause of blindness in patients over the age of 50. It is characterized by progressive degeneration of the photoreceptors, outer retina, and retinal pigment epithelium at the macula. There are two types of AMD: dry and wet AMD. Most AMD starts as the dry type and in 10-20% of individuals, it progresses to the wet type. Wet AMD frequently causes a rapid and often substantial loss of central vision in patients. In the wet form of AMD, choroidal neovascularization forms and develops into a network of vessels that may grow under and through the retinal pigment epithelium. As this is accompanied by leakage of plasma and/or hemorrhage into the subretinal space, severe and sudden loss of central vision may result. While wet AMD affects approximately 10-20% of individuals with age-related macular degeneration, it accounts for approximately 90% of all cases of severe vision loss from the disease. AMD has been shown to have no single cause, and likely results from variable contributions including but not limited to age, genetic predisposition, and/or environmental factors. In humans, for example, established epidemiologic risk factors may include but are not limited to cigarette smoking, diet, female sex, Caucasian race, and a family history of AMD.

Pathological myopia (also known as high myopia or degenerative myopia) is another leading cause of visual impairment worldwide and is the most frequent cause of visual impairment in Asian countries. It is a form of severe and progressive nearsightedness characterized by changes in the fundus of the eye, due to posterior staphyloma and deficient corrected acuity. Other ocular diseases that are significant causes of loss of vision worldwide include, for example, diabetic retinopathy, hereditary retinal dystrophies, proliferative vitreoretinopathy, retinopathy of prematurity, diabetic macular oedema, neovascular glaucoma and Coats' disease.

Anti-VEGF agents (e.g. anti-VEGF antibodies, VEGF Traps, etc.) are now widely used in the treatment of ocular diseases such as wet AMD, diabetic retinopathy, diabetic macular edema, pathological myopia (particularly those pathological myopia patients presenting with choroidal neovascularization (CNV)) and other ocular diseases, and function to inhibit neovascularization and angiogenesis. In most patients this can reduce the progression of choroidal neovascularization and vision loss resulting from the downstream effects of neovascularization, and has been observed to reduce some aspects of inflammation in animal models. For example anti-VEGFs may modify the retinal damage induced by neovascularization and therefore resolve follow-on inflammatory activities by immune cells. However, anti-VEGF agents will not block proinflammatory cytokine release from an already activated immune cell (see e.g. Funk et al., 2010, Retina, 30(9):1412-1419). Despite regular (e.g. monthly) injections of anti-VEGF agents, many patients with ocular disease still proceed to lose their vision due to the development of fibrotic lesions and atrophy. In wet-AMD some patients continue to loose visual acuity over 5 years even with sustained treatment. In addition, some 10-15% of patients don't respond to anti-VEGF therapies. Other ocular diseases, have no approved pharmacologic treatment available for use. Accordingly, there remains a need for additional agents and methods for treating ocular diseases.

SUMMARY OF THE INVENTION

The present invention arises in part from the surprising determination that targeting Cluster of Differentiation 14 (CD14), such as by administration of an anti-CD14 antagonist antibody, is particularly efficient at reducing not only neovascularization and lesion size, but also fibrosis in a laser-induced mouse model of choroidal neovascularization (CNV), and is associated with a reduction of vascular endothelial growth factor (VEGF) in the retinal pigment epithelium (RPE). This is in contrast to gold-standard anti-VEGF therapy (e.g. aflibercept, a VEGF-Trap that is the standard of care for many ocular diseases such as AMD), which at high doses inhibits neovascularization and reduces lesion size but does not inhibit fibrosis and indeed is associated with an increased expression in the RPE of VEGF isoforms and other genes associated with the formation of extracellular matrix.

Interestingly, the unexpected reduction in fibrosis in the retina following anti-CD14 treatment appears to be through a novel mechanism that is not related to lesion size (i.e. not related to angiogenesis/neovascularisation): inhibition of fibrosis following treatment with anti-CD14 antibody was uniform and irrespective of the inhibition of lesion size, and VEGF protein levels were reduced in the RPE but not the retina, suggesting that this was through antagonism of the mCD14 receptors expressed on the RPE and not anti-CD14 attenuation of infiltrating macrophage activity. Thus, the unexpected anti-fibrotic activity of the anti-CD14 antibody following laser-induced CNV is independent of its anti-inflammatory and anti-angiogenic (i.e. anti-neovascularisation) activity.

The surprising finding by the present inventors that targeting CD14 can inhibit not only neovascularization (or angiogenesis) in a mouse model of CNV but can also inhibit fibrosis has significant implications for the treatment of ocular diseases, many of which are characterized by neovascularization and fibrosis and thus will be amenable to treatment with a CD14 antagonist antibody. Of particular note is the fact that current therapies, while able to inhibit neovascularization, do not necessarily also inhibit fibrosis. Indeed, it has been reported that 40-50% of patients with wet AMD go blind due to ocular fibrosis even when treated with anti-VEGF therapies. In the Comparison of Age-related Macular Degeneration Treatments Trials (CATT), it was observed that following a year of anti-VEGF treatment, 32% of patients developed fibrotic scars after a further year, with 42% and 56% developing fibrotic scars after a further 2 and 5 years, respectively, even while being successfully treated for neovascularization (i.e. fibrosis can develop in this disease state independently of neovascularization). During this period of fibrosis development, visual acuity decreased (Daniel et al., 2018, Ophthalmology 125(7): 1037-1046). Indeed, it has been postulated that treatment with anti-VEGF agents may actually promote fibrosis. Treatment with a CD14 antagonist antibody as described herein to patients that are receiving or have received anti-VEGF treatment can therefore inhibit the development of fibrosis, as well as the separate processes of ocular inflammation and neovascularization, and aid in the retention of vision for patients with AMD and other ocular diseases that are characterized by fibrosis, inflammation and neovascularization.

Thus, in one aspect, provided is a method for treating an ocular disease or disorder in a subject, comprising, consisting or consisting essentially of administering an effective amount of a CD14 antagonist antibody to a subject with an ocular disease or disorder. In another aspect, provided is a method for inhibiting ocular inflammation, neovascularization and/or fibrosis in a subject with an ocular disease or disorder, comprising, consisting or consisting essentially of administering an effective amount of a CD14 antagonist antibody to a subject with an ocular disease or disorder. The ocular disease may be selected from among, for example, pathological myopia, AMD, diabetic retinopathy, hereditary retinal dystrophies, proliferative vitreoretinopathy, retinopathy of prematurity, diabetic macular oedema, neovascular glaucoma, dry eye, fibrosis associated with glaucoma filtration surgery (GFS), Coats' disease, non-infectious uveitis (NIU), macular telangiectasia (MacTel), cystoid macular edema, birdshot chorioretinopathy, Vogt-Koyanagi-Harada disease, idiopathic multifocal choroiditis, retinal vasculitis, branched vein retinal occlusions (BRVO) and central vein retinal occlusions (CRVO), polypoidal choroidal vasculopathy, Familial Exudative Vitreoretinopathy (FEVR), Idiopathic retinitis, Vasculitis, Aneurysms, and Neuroretinitis (IRVAN), Doyone honeycomb retinal dystrophy, and enhanced S-cone syndrome. In further examples, the method comprises first selecting the subject for administration of the CD14 antagonist antibody on the basis that the subject is at risk of developing, or has, ocular fibrosis (e.g. retinal, subretinal or epiretinal fibrosis). In some embodiments, the AMD is wet AMD or dry AMD.

In another aspect, provided is a method for treating AMD in a subject, comprising, consisting or consisting essentially of: selecting a subject with AMD who is at risk of developing, or has, ocular fibrosis (e.g. retinal, subretinal or epiretinal fibrosis); and administering an effective amount of a CD14 antagonist antibody to the subject. In another aspect, provided is a method for inhibiting ocular fibrosis in a subject with AMD, comprising, consisting or consisting essentially of: selecting a subject with AMD who is at risk of developing, or has, ocular fibrosis (e.g. retinal, subretinal or epiretinal fibrosis); and administering an effective amount of a CD14 antagonist antibody to the subject. In some embodiments, the AMD is wet AMD or dry AMD.

In another aspect, provided is a use of a CD14 antagonist antibody for the preparation of a medicament for treating an ocular disease or disorder in a subject, or for inhibiting ocular inflammation, neovascularization and/or fibrosis in a subject with an ocular disease or disorder. In some examples, the ocular disease or disorder is selected from among pathological myopia, AMD, diabetic retinopathy, hereditary retinal dystrophies, proliferative vitreoretinopathy, retinopathy of prematurity, diabetic macular oedema, neovascular glaucoma, dry eye, fibrosis associated with glaucoma filtration surgery (GFS), Coats' disease, non-infectious uveitis (NIU), macular telangiectasia (MacTel), cystoid macular edema, birdshot chorioretinopathy, Vogt-Koyanagi-Harada disease, idiopathic multifocal choroiditis, retinal vasculitis, branched vein retinal occlusions (BRVO) and central vein retinal occlusions (CRVO), polypoidal choroidal vasculopathy, Familial Exudative Vitreoretinopathy (FEVR), Idiopathic retinitis, Vasculitis, Aneurysms, and Neuroretinitis (IRVAN), Doyone honeycomb retinal dystrophy, and enhanced S-cone syndrome. In further examples, the method comprises first selecting the subject for administration of the CD14 antagonist antibody on the basis that the subject is at risk of developing, or has, ocular fibrosis (e.g. retinal, subretinal or epiretinal fibrosis). In some embodiments, the AMD is wet AMD or dry AMD.

In another aspect, provided is a use of a CD14 antagonist antibody for the preparation of a medicament for treating AMD in a subject identified as being at risk of developing, or having, ocular fibrosis. In a further aspect, provided is a use of a CD14 antagonist antibody for the preparation of a medicament for inhibiting ocular inflammation in a subject with AMD identified as being at risk of developing, or having, ocular fibrosis. In some examples, the AMD is wet AMD or dry AMD.

In some embodiments of the methods and uses, the subject has received an anti-VEGF agent for at least 3, 6, 9, 12, 14, 16 or 18 months. In further examples, the subject is a non-responder to anti-VEGF agent. The anti-VEGF agent may be, for example, an anti-VEGF antibody (e.g. brolicizumab, ranibizumab or faricimab), anti-VEGF antibody mimetic (e.g. abicipar pegol), VEGF Trap molecule (e.g. aflibercept or conbercept), soluble fms-like tyrosine kinase-1, or a tyrosine kinase inhibitor.

In particular embodiments, the subject is determined to have ocular fibrosis by detection of the presence of hyper-reflective material (HRM) by optical coherence tomography (OCT).

In other embodiments, the subject is determined to have ocular fibrosis by confirming the presence of fibrotic lesions by visualization using fluorescein angiography, color fundus photography (CFP) or fundus autofluorescence (FAF).

The CD14 antagonist antibody may be administered by local ocular administration, systemic administration or topical administration. In some examples, the CD14 antagonist antibody is administered by ocular implantation.

In one embodiment, the CD14 antagonist antibody is selected from:

(i) an antibody that comprises: a) an antibody VL domain, or antigen binding fragment thereof, comprising L-CDR1, L-CDR2 and L-CDR3, wherein: L-CDR1 comprises the sequence RASESVDSFGNSFMH [SEQ ID NO: 7] (3C10 L-CDR1); L-CDR2 comprises the sequence RAANLES [SEQ ID NO: 8] (3C10 L-CDR2); and L-CDR3 comprises the sequence QQSYEDPWT [SEQ ID NO: 9](3C10 L-CDR3); and b) an antibody VH domain, or antigen binding fragment thereof, comprising H-CDR1, H-CDR2 and H-CDR3, wherein: H-CDR1 comprises the sequence SYAMS [SEQ ID NO: 10](3C10 H-CDR1); H-CDR2 comprises the sequence SISSGGTTYYPDNVKG [SEQ ID NO: 11] (3C10 H-CDR2); and H-CDR3 comprises the sequence GYYDYHY [SEQ ID NO: 12] (3C10 H-CDR3);

(ii) an antibody that comprises: a) an antibody VL domain, or antigen binding fragment thereof, comprising L-CDR1, L-CDR2 and L-CDR3, wherein: L-CDR1 comprises the sequence RASESVDSYVNSFLH [SEQ ID NO: 13] (28C5 L-CDR1); L-CDR2 comprises the sequence RASNLQS [SEQ ID NO: 14] (28C5 L-CDR2); and L-CDR3 comprises the sequence QQSNEDPTT [SEQ ID NO: 15] (28C5 L-CDR3); and b) an antibody VH domain, or antigen binding fragment thereof, comprising H-CDR1, H-CDR2 and H-CDR3, wherein: H-CDR1 comprises the sequence SDSAWN [SEQ ID NO: 16] (28C5 H-CDR1); H-CDR2 comprises the sequence YISYSGSTSYNPSLKS [SEQ ID NO: 17] (28C5 H-CDR2); and H-CDR3 comprises the sequence GLRFAY [SEQ ID NO: 18] (28C5 H-CDR3);

(iii) an antibody that comprises: a) an antibody VL domain, or antigen binding fragment thereof, comprising L-CDR1, L-CDR2 and L-CDR3, wherein: L-CDR1 comprises the sequence RASESVDSYVNSFLH [SEQ ID NO: 13] (IC14 L-CDR1); L-CDR2 comprises the sequence RASNLQS [SEQ ID NO: 14] (IC14 L-CDR2); and L-CDR3 comprises the sequence QQSNEDPYT [SEQ ID NO: 27] (IC14 L-CDR3); and b) an antibody VH domain, or antigen binding fragment thereof, comprising H-CDR1, H-CDR2 and H-CDR3, wherein: H-CDR1 comprises the sequence SDSAWN [SEQ ID NO: 16] (IC14 H-CDR1); H-CDR2 comprises the sequence YISYSGSTSYNPSLKS [SEQ ID NO: 17] (IC14 H-CDR2); and H-CDR3 comprises the sequence GLRFAY [SEQ ID NO: 18] (IC14 H-CDR3); and (iv) an antibody that comprises: a) an antibody VL domain, or antigen binding fragment thereof, comprising L-CDR1, L-CDR2 and L-CDR3, wherein: L-CDR1 comprises the sequence RASQDIKNYLN [SEQ ID NO: 19] (18E12 L-CDR1); L-CDR2 comprises the sequence YTSRLHS [SEQ ID NO: 20] (18E12 L-CDR2); and L-CDR3 comprises the sequence QRGDTLPWT [SEQ ID NO: 21](18E12 L-CDR3); and b) an antibody VH domain, or antigen binding fragment thereof, comprising H-CDR1, H-CDR2 and H-CDR3, wherein: H-CDR1 comprises the sequence NYDIS [SEQ ID NO: 22](18E12 H-CDR1); H-CDR2 comprises the sequence VIWTSGGTNYNSAFMS [SEQ ID NO: 23] (18E12 H-CDR2); and H-CDR3 comprises the sequence GDGNFYLYNFDY [SEQ ID NO: 24] (18E12 H-CDR3).

In another embodiment, the CD14 antagonist antibody is selected from:

(i) an antibody comprising:
a VL domain that comprises, consists or consists essentially of the sequence:

(3C10 VL)
[SEQ ID NO: 1]
QSPASLAVSLGQRATISCRASESVDSFGNSFMHWYQQKAGQPPKSSIYRA

ANLESGIPARFSGSGSRTDFTLTINPVEADDVATYFCQQSYEDPWTFGGG

TKLGNQ;

and
a VH domain that comprises, consists or consists essentially of the sequence:

(3C10 VH)
[SEQ ID NO: 2]
LVKPGGSLKLSCVASGFTFSSYAMSWVRQTPEKRLEWVASISSGGTTYYP

DNVKGRFTISRDNARNILYLQMSSLRSEDTAMYYCARGYYDYHYWGQGTT

LTVSS;

(ii) an antibody comprising:
a VL domain that comprises, consists or consists essentially of the sequence:

(28C5 VL)
[SEQ ID NO: 3]
QSPASLAVSLGQRATISCRASESVDSYVNSFLHWYQQKPGQPPKLLIYRA

SNLQSGIPARFSGSGSRTDFTLTINPVEADDVATYCCQQSNEDPTTFGGG

TKLEIK;

and
a VH domain that comprises, consists or consists essentially of the sequence:

(28C5 VH)
[SEQ ID NO: 4]
LQQSGPGLVKPSQSLSLTCTVTGYSITSDSAWNWIRQFPGNRLEWMGYIS

YSGSTSYNPSLKSRISITRDTSKNQFFLQLNSVTTEDTATYYCVRGLRFA

YWGQGTLVTVSA;

(iii) an antibody comprising:
a VL domain that comprises, consists or consists essentially of the sequence:

(IC14 VL)
[SEQ ID NO: 25]
QSPASLAVSLGQRATISCRASESVDSYVNSFLHWYQQKPGQPPKLLIYRA

SNLQSGIPARFSGSGSRTDFTLTINPVEADDVAMCQQSNEDPYTFGGGTK

LEIK;

and
a VH domain that comprises, consists or consists essentially of the sequence:

(IC14 VH)
[SEQ ID NO: 26]
LQQSGPGLVKPSQSLSLTCTVTGYSITSDSAWNWIRQFPGNRLEWMGYIS

YSGSTSYNPSLKSRISITRDTSKNQFFLQLNSVTTEDTAMCVRGLRFAYW

GQGTLVTVSS;

and (iv) an antibody comprising:

a VL domain that comprises, consists or consists essentially of the sequence:

```
(18E12 VL)
                                     [SEQ ID NO: 5]
QTPSSLSASLGDRVTISCRASQDIKNYLNWYQQPGGTVKVLIYYTSRLHS

GVPSRFSGSGSGTDYSLTISNLEQEDFATYFCQRGDTLPWTFGGGTKLEI

K;
``` and a VH domain that comprises, consists or consists essentially of the sequence:

```
(18E12 VH)
                                     [SEQ ID NO: 6]
LESGPGLVAPSQSLSITCTVSGFSLTNYDISWIRQPPGKGLEWLGVIWTS

GGTNYNSAFMSRLSITKDNSESQVFLKMNGLQTDDTGIYYCVRGDGNFYL

YNFDYWGQGTTLTVSS.
```

In some examples, the CD14 antagonist antibody is humanized or chimeric. In a particular example, the CD14 antagonist antibody comprises:

```
a light chain comprising the amino acid
sequence
                                     [SEQ ID NO: 32]
DIVLTQSPASLAVSLGQRATISCRASESVDSYVNSFLHWYQQKPGQPPKL

LIYRASNLQSGIPARFSGSGSRTDFTLTINPVEADDVATYYCQQSNEDPY

TFGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC;
and
a heavy chain comprising the amino acid
sequence:
                                     [SEQ ID NO: 33]
DVQLQQSGPGLVKPSQSLSLTCTVTGYSITSDSAWNWIRQFPGNRLEWMG

YISYSGSTSYNPSLKSRISITRDTSKNQFFLQLNSVTTEDTATYYCVRGL

RFAYWGQGTLVTVSSASTKGPSVFPLAPCSRSTSESTAALGCLVKDYFPE

PVTVSWNSGALTSGVHTFPAVLQSSGLYSLSSVVTVPSSSLGTKTYTCNV

DHKPSNTKVDKRVESKYGPPCPSCPAPEFLGGPSVFLFPPKPKDTLMISR

TPEVTCVVVDVSQEDPEVQFNWYVDGVEVHNAKTKPREEQFNSTYRVVSV

LTVLHQDWLNGKEYKCKVSNKGLPSSIEKTISKAKGQPREPQVYTLPPSQ

EEMTKNQVSLTCLVKGFYPSDIAVEWESNGQPENNYKTTPPVLDSGSFF

LYSRLTVDKSRWQEGNVFSCSVMHEALHNHYTQKSLSLSLGK.
```

The CD14 antagonist antibody may be administered in combination with, or formulated for use in combination with, an ancillary agent. In some examples, the CD14 antagonist antibody and the ancilliary agent are administered simultaneously or sequentially. In particular examples, the ancillary agent is selected from among an anti-VEGF agents, and angiotensin converting enzyme (ACE) inhibitor, a connective tissue growth factor (CTGF) inhibitor, a complement inhibitor (e.g. a C3, C5, factor B, factor D, or properdin inhibitor), an angiopoietin 2 (Ang-2) inhibitor, a PDGF inhibitor, a statin, and a steroid. The anti-VEGF agent may be selected from among an anti-VEGF antibody (e.g. brolicizumab, ranibizumab or faricimab), anti-VEGF antibody mimetic (e.g. abicipar pegol), VEGF Trap molecule (e.g. aflibercept or conbercept), soluble fms-like tyrosine kinase-1, and a tyrosine kinase inhibitor.

BRIEF DESCRIPTION OF THE DRAWINGS

Embodiments of the disclosure are described herein, by way of non-limiting example only, with reference to the following drawings.

DETAILED DESCRIPTION OF THE INVENTION

1. Definitions

Figure 1:
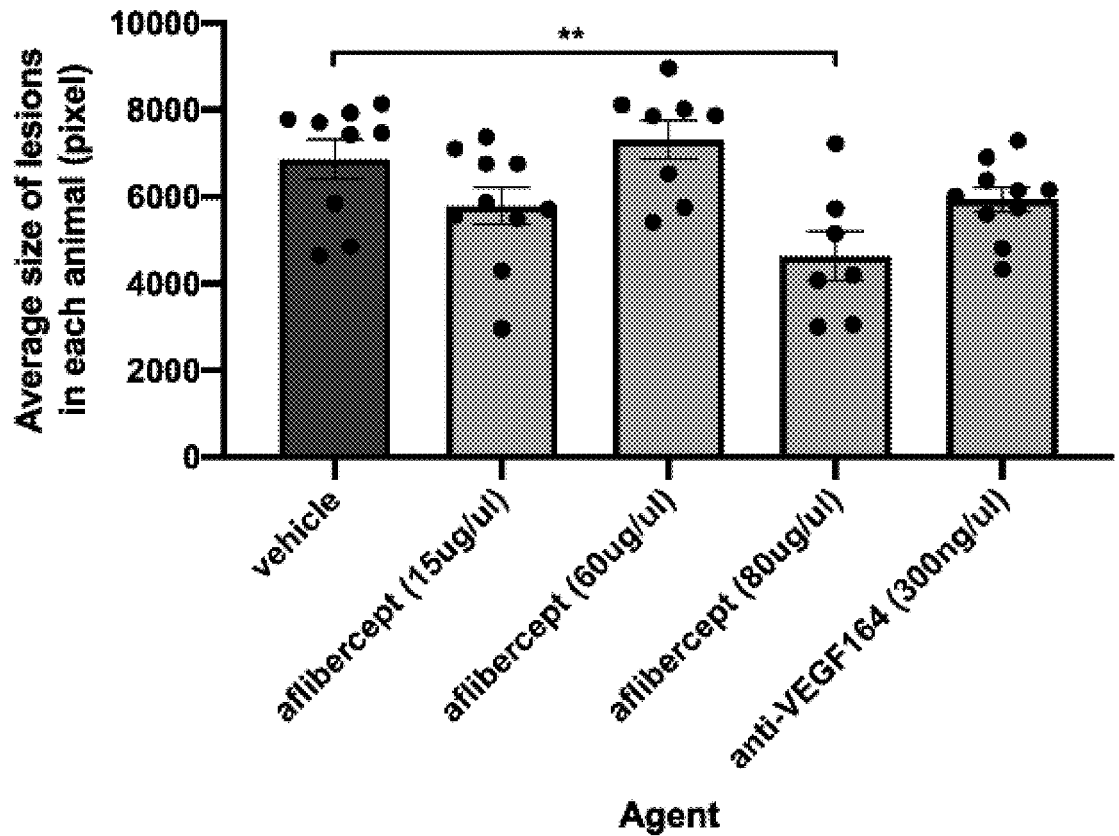
FIG. 1 is a graphical representation of angiogenesis seven days after laser induced choroidal neovascularization. (A) Graph of mean+SEM lesion size in eyes treated with different concentrations of aflibercept (15ug/µl, 60 ug/µl or 80 µg/ml), vehicle or anti-VEGF164 neutralizing antibody (300 ng/ul). (B) Graph of mean±SEM lesion size in eyes treated with aflibercept (80 ul/ml), anti-CD14 or vehicle. One-way ANOVA, post-hoc Tukey's test, ** $p<0.01$, n≥8.
Figure 1:
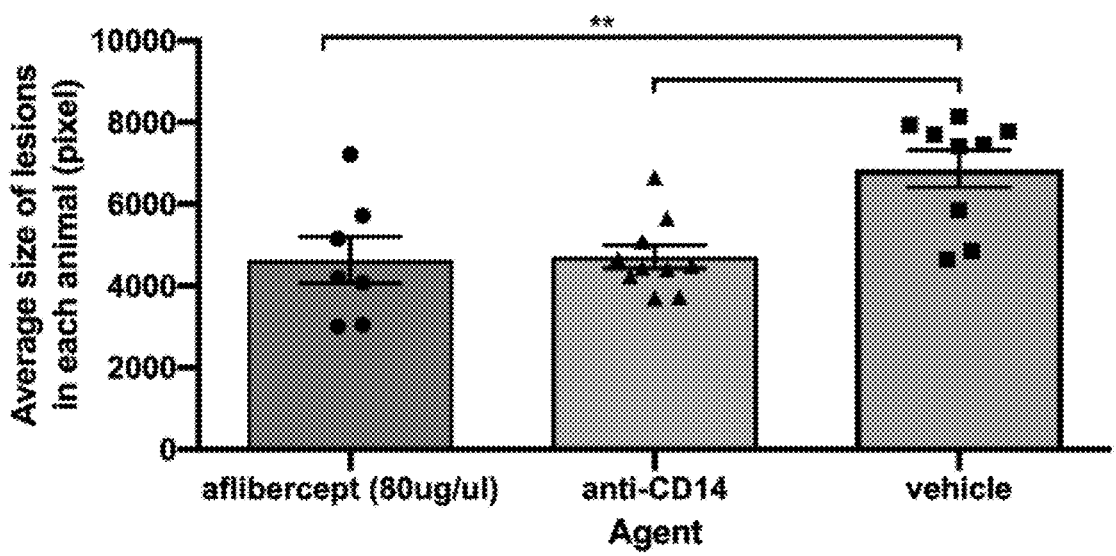

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

As used herein, "and/or" refers to and encompasses any and all possible combinations of one or more of the associated listed items, as well as the lack of combinations when interpreted in the alternative (or).

The terms "active agent" and "therapeutic agent" are used interchangeably herein and refer to agents that prevent, reduce or ameliorate at least one symptom of a disease or disorder.

The terms "administration concurrently" or "administering concurrently" or "co-administering" and the like refer to the administration of a single composition containing two or more agents, or the administration of each agent as separate compositions and/or delivered by separate routes either contemporaneously or simultaneously or sequentially within a short enough period of time that the effective result is equivalent to that obtained when all such agents are administered as a single composition. By "simultaneously" is meant that the agents are administered at substantially the same time, and desirably together in the same formulation. By "contemporaneously" it is meant that the agents are administered closely in time, e.g., one agent is administered within from about one minute to within about one day before or after another. Any contemporaneous time is useful. However, it will often be the case that when not administered simultaneously, the agents will be administered within about one minute to within about eight hours and suitably within less than about one to about four hours. When administered contemporaneously, the agents are suitably administered at the same site on the subject. The term "same site" includes the exact location, but can be within about 0.5 to about 15 centimeters, preferably from within about 0.5 to about 5 centimeters. The term "separately" as used herein means that the agents are administered at an interval, for example at an interval of about a day to several weeks or months. The agents may be administered in either order. The term "sequentially" as used herein means that the agents are administered in sequence, for example at an interval or intervals of minutes, hours, days or weeks. If appropriate the agents may be administered in a regular repeating cycle.

The term "antagonist antibody" is used in the broadest sense, and includes an antibody that inhibits or decreases the biological activity of an antigen to which the antibody binds (e.g., CD14). For example, an antagonist antibody may partially or completely block interaction between a receptor (e.g., CD14) and a ligand (e.g., a DAMP or PAMP), or may practically decrease the interaction due to tertiary structure change or down regulation of the receptor. Thus, a CD14 antagonist antibody encompasses antibodies that bind to CD14 and that block, inhibit, nullify, antagonize, suppress, decrease or reduce (including significantly), in any meaningful degree, a CD14 agonist activity, including activation of downstream pathways such as Toll-like receptor (TLR) signaling pathways (e.g., TLR4 signaling pathway) and the TIR-domain-containing adapter-inducing IFN-β (TRIF) pathway, or elicitation of a cellular response (e.g., production of pro-inflammatory mediators including pro-inflammatory cytokines) to CD14 binding by a CD14 ligand (e.g., a DAMP or PAMP).

The term "antibody" herein is used in the broadest sense and specifically covers naturally occurring antibodies, monoclonal antibodies, polyclonal antibodies, multispecific antibodies (e.g., bispecific antibodies), antibody fragments, or any other antigen-binding molecule so long as they exhibit the desired immuno-interactivity. A naturally occurring "antibody" includes within its scope an immunoglobulin comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised specific CH domains (e.g., CH1, CH2 and CH3). Each light chain is comprised of a light chain variable region (abbreviated herein as VL) and a light chain constant region. The light chain constant region is comprised of one domain, CL. The VH and VL regions can be further subdivided into regions of hypervariability, termed complementary determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The constant regions of the antibodies may mediate the binding of an immunoglobulin to host tissues or factors, including various cells of the immune system (e.g., effector cells) and the first component (C1q) of the classical complement system. The antibodies can be of any isotype (e.g., IgG, IgE, IgM, IgD, IgA and IgY), class (e.g., IgG1, IgG2, IgG3, IgG4, IgA1 and IgA2), subclass or modified version thereof (e.g., IgG1 isotype, which carries L234A and L235A double mutations (IgG1-LALA)). The antibodies can be of any species, chimeric, humanized or human. In other embodiments, the antibody is a homomeric heavy chain antibody (e.g., camelid antibodies) which lacks the first constant region domain (CH1) but retains an otherwise intact heavy chain and is able to bind antigens through an antigen-binding domain. The variable regions of the heavy and light chains in the antibody-modular recognition domain (MRD) fusions will contain a functional binding domain that interacts with an antigen of interest.

The "variable domain" (variable domain of a light chain (VL), variable domain of a heavy chain (VH)) as used herein denotes each of the pair of light and heavy chain domains which are involved directly in binding the antibody to the antigen. The variable light and heavy chain domains have the same general structure and each domain comprises four FRs whose sequences are widely conserved, connected by three CDRs or "hypervariable regions". The FRs adopt a p-sheet conformation and the CDRs may form loops connecting the p-sheet structure. The CDRs in each chain are held in their three-dimensional structure by the FRs and form together with the CDRs from the other chain the antigen binding site.

The term "antigen-binding portion" when used herein refer to the amino acid residues of an antibody which are responsible for antigen-binding generally, which generally comprise amino acid residues from the CDRs. Thus, "CDR" or "complementarity determining region" (also referred to as "hypervariable region") are used interchangeably herein to refer to the amino acid sequences of the light and heavy chains of an antibody which form the three-dimensional loop structure that contributes to the formation of an antigen binding site. There are three CDRs in each of the variable regions of the heavy chain and the light chain, which are designated "CDR1", "CDR2", and "CDR3", for each of the variable regions. The term "CDR set" as used herein refers to a group of three CDRs that occur in a single variable region that binds the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, 1987. *J. Mol. Biol.* 196: 901-917; Chothia et al., 1989. *Nature* 342: 877-883) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan (1995. *FASEB J.* 9: 133-139) and MacCallum (1996. *J. Mol. Biol.* 262(5): 732-745). Still other CDR boundary definitions may not strictly follow one of these systems, but will nonetheless overlap with the Kabat CDRs, although they may be shortened or lengthened in light of prediction or experimental findings that particular residues or groups of residues or even entire CDRs do not significantly impact antigen binding.

As used herein, the term "framework region" or "FR" refers to the remaining sequences of a variable region minus the CDRs. Therefore, the light and heavy chain variable domains of an antibody comprise from N- to C-terminus the domains FR1, CDR1, FR2, CDR2, FR3, CDR3, and FR4. CDRs and FRs are typically determined according to the standard definition of Kabat, E. A., et al., Sequences of Proteins of Immunological Interest, 5th ed., Public Health Service, National Institutes of Health, Bethesda, Md. (1991) and/or those residues from a "hypervariable loop".

As used herein, the terms "light chain variable region" ("VL") and "heavy chain variable region" (VH) refer to the regions or domains at the N-terminal portion of the light and heavy chains respectively which have a varied primary amino acid sequence for each antibody. The variable region of an antibody typically consists of the amino terminal domain of the light and heavy chains as they fold together to form a three-dimensional binding site for an antigen. Several subtypes of VH and VL, based on structural similarities, have been defined, for example as set forth in the Kabat database.

The term "chimeric antibody" refers to antibodies that comprise heavy and light chain variable region sequences from one species and constant region sequences from another species, such as antibodies having murine heavy and light chain variable regions linked to human constant regions.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Thus, the FRs and CDRs of a humanized antibody need not correspond precisely to the parental (i.e., donor) sequences, e.g., a donor antibody CDR or the consensus framework may be mutagenized by substitution, insertion, and/or deletion of at least one amino acid residue so that the CDR or FR at that site does not correspond to either the donor antibody or the consensus framework. Typically, such mutations, however, will not be extensive and will generally avoid "key residues" involved in binding to an antigen. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, for example, Winnaker, *From Genes to Clones* (Verlagsgesellschaft, Weinheim, 1987)). A "consensus immunoglobulin sequence" may thus comprise a "consensus framework region(s)" and/or a "consensus CDR(s)". In a family of immunoglobulins, each position in the consensus sequence is occupied by the amino acid occurring most frequently at that position in the family. If two amino acids occur equally frequently, either can be included in the consensus sequence. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will generally comprise at least a portion of an immunoglobulin constant region (Fc), typically that of a human immunoglobulin. For further details, see Jones et al. (1986. *Nature* 321:522-525), Riechmann et al. (1988. *Nature* 332:323-329) and Presta (1992. *Curr. Op. Struct. Biol.* 2:593-596). A humanized antibody can be selected from any class of immunoglobulins, including IgM, IgG, IgD, IgA, and IgE, and any isotype, including without limitation IgG1, IgG2, IgG3, and IgG4. A humanized antibody may comprise sequences from more than one class or isotype, and particular constant domains may be selected to optimize desired effector functions using techniques well known in the art. As used herein, the term "key residue" refers to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, "Vernier" zone refers to a subset of framework residues that may adjust CDR structure and fine-tune the fit to antigen as described by Foote and Winter (1992. *J. Mol. Biol.* 224: 487-499). Vernier zone residues form a layer underlying the CDRs and may impact on the structure of CDRs and the affinity of the antibody.

As used herein, the term "canonical" residue refers to a residue in a CDR or framework that defines a particular canonical CDR structure as defined by Chothia et al. (1987. *J. Mol. Biol.* 196: 901-917; 1992. *J. Mol. Biol.* 227: 799-817), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs to an "acceptor antibody". In some embodiments, the donor antibody is an antibody from a species different from the antibody from which the FRs are obtained or derived. In the context of a humanized antibody, the term "donor antibody" refers to a non-human antibody providing one or more CDRs.

As used herein, the terms "acceptor" and "acceptor antibody" refer to an antibody providing at least 80%, at least 85%, at least 90%, at least 95%, at least 98%, or 100% of the amino acid sequences of one or more of the FRs. In some embodiments, the term "acceptor" refers to the antibody amino acid sequence providing the constant region(s). In other embodiments, the term "acceptor" refers to the antibody amino acid sequence providing one or more of the FRs and the constant region(s). In specific embodiments, the term "acceptor" refers to a human antibody amino acid sequence that provides at least 80%, preferably, at least 85%, at least 90%, at least 95%, at least 98%, or 100% of the amino acid sequences of one or more of the FRs. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, for example, derived or obtained from a germline antibody gene, a mature antibody gene, a functional antibody (e.g., antibodies well-known in the art, antibodies in development, or antibodies commercially available).

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The terms "heavy chain variable region CDR1" and "H-CDR1" are used interchangeably, as are the terms "heavy chain variable region CDR2" and "H-CDR2", the terms "heavy chain variable region CDR3" and "H-CDR3", the terms "light chain variable region CDR1" and "L-CDR1"; the terms "light chain variable region CDR2" and "L-CDR2" and the terms "light chain variable region CDR3" and "L-CDR3" antibody fragment. Throughout the specification, complementarity determining regions ("CDR") are defined according to the Kabat definition unless specified otherwise. The Kabat definition is a standard for numbering the residues in an antibody and it is typically used to identify CDR regions (Kabat et al., (1991), 5th edition, NIH publication No. 91-3242).

Antigen binding can be performed by "fragments" or "antigen-binding fragments" of an intact antibody. Herein, both terms are used interchangeably. Examples of binding fragments encompassed within the term "antibody fragment" of an antibody include a Fab fragment, a monovalent fragment consisting of the VL, VH, CL and CH1 domains; a F(ab')2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989. *Nature* 341:544-546), which consists of a VH domain; and an isolated complementary determining region (CDR). In a particular embodiment, the antibody of the present disclosure is an antigen-binding fragment that lacks all or a portion of the Fc region.

A "single chain variable Fragment (scFv)" is a single protein chain in which the VL and VH regions pair to form monovalent molecules (known as single chain Fv (scFv); see, e.g., Bird et al., 1988. *Science* 242:423-426; and Huston et al., 1988. Proc. Natl. Acad. Sci. 85:5879-5883). Although the two domains VL and VH are coded for by separate genes, they can be joined, using recombinant methods, by an artificial peptide linker that enables them to be made as a single protein chain. Such single chain antibodies include one or more antigen binding moieties. These antibody fragments are obtained using conventional techniques known to those of skill in the art, and the fragments are screened for utility in the same manner as are intact antibodies.

The term "monoclonal antibody" and abbreviations "MAb" and "mAb", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each mAb is directed against a single determinant on the antigen. The modifier "monoclonal" is not to be construed as requiring production of the antibody by any particular method. Monoclonal antibodies may be produced, for example, by a single clone of antibody-producing cells, including hybridomas. The term "hybridoma" generally refers to the product of a cell-fusion between a cultured neoplastic lymphocyte and a primed B- or T-lymphocyte which expresses the specific immune potential of the parent cell.

An antibody "that binds" an antigen of interest (e.g., CD14) is one that binds the antigen with sufficient affinity such that the antibody is useful as a therapeutic agent in targeting a cell or tissue expressing the antigen, and does not significantly cross-react with other proteins. In such embodiments, the extent of binding of the antibody to a "non-target" protein will be less than about 10% of the binding of the antibody, oligopeptide or other organic molecule to its particular target protein as determined, for example, by fluorescence activated cell sorting (FACS) analysis, enzyme-linked immunosorbent assay (ELISA), immunoprecipitation or radioimmunoprecipitation (RIA). Thus, an antibody that antagonizes CD14 suitably inhibits or decreases production of pro-inflammatory mediators, including pro-inflammatory cytokines/chemokines. With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The specific region of the antigen to which the antibody binds is typically referred to as an "epitope". The term "epitope" broadly includes the site on an antigen which is specifically recognized by an antibody or T-cell receptor or otherwise interacts with a molecule. Generally epitopes are of active surface groupings of molecules such as amino acids or carbohydrate or sugar side chains and generally may have specific three-dimensional structural characteristics, as well as specific charge characteristics. As will be appreciated by one of skill in the art, practically anything to which an antibody can specifically bind could be an epitope.

An "anti-VEGF agent" (or VEGF inhibitor or VEGF antagonist) refers to a molecule capable of neutralizing, blocking, inhibiting, abrogating, reducing or interfering with an activity of vascular endothelial growth factor (VEGF), including but not limited to its binding to one or more VEGF receptors. Anti-VEGF agents include anti-VEGF antibodies including antigen-binding fragments thereof, receptor molecules and derivatives which bind specifically to VEGF thereby sequestering its binding to one or more receptors (e.g. VEGF Traps), anti-VEGF receptor antibodies and VEGF receptor antagonists such as small molecule inhibitors of the VEGFR tyrosine kinases, and fusions proteins. By way of example, exemplary anti-VEGF agents include the anti-VEGF antibodies bevacizumab and ranibizumab, the VEGF Trap aflibercept (also referred to as VEGF Trap Eye), and small molecules such as lapatinib, sunitinib, sorafenib, axitinib, and pazopanib that inhibit the tyrosine kinases stimulated by VEGF. "Anti-VEGF therapy" refers to a treatment regimen using an anti-VEGF agent.

Throughout this specification, unless the context requires otherwise, the words "comprise", "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

By "effective amount", in the context of treating a disease or condition is meant the administration of an amount of an agent or composition to an individual in need of such treatment or prophylaxis, either in a single dose or as part of a series, that is effective for the prevention of incurring a symptom, holding in check such symptoms, and/or treating existing symptoms, of that condition. The effective amount will vary depending upon the age, health and physical condition of the individual to be treated and whether symptoms of disease are apparent, the taxonomic group of individual to be treated, the formulation of the composition, the assessment of the medical situation, and other relevant factors. Optimal dosing schedules can be calculated from measurements of drug accumulation in the body of the subject. Optimum dosages may vary depending on the relative potency in an individual subject, and can generally be estimated based on EC50 values found to be effective in in vitro and in vivo animal models. Persons of ordinary skill can easily determine optimum dosages, dosing methodologies and repetition rates. It is expected that the amount will fall in a relatively broad range that can be determined through routine trials.

The terms "inhibit" or "reduce" and the like in relation to ocular inflammation, neovascularization or fibrosis or loss of vision refers to at least a small but measurable inhibition or reduction in ocular inflammation, neovascularization or fibrosis or loss of vision of a subject with an ocular disease following administration of an anti-CD14 antagonist antibody, compared to in the absence of administration of the antibody. Typically, the inhibition or decrease is a statistically significant inhibition or decrease. In some embodiments, ocular inflammation, neovascularization or fibrosis or loss of vision is decreased or inhibited by at least 10%, 20%, 30%, 40%, 50%, 60%, 70%, 80%, or more. In one example, loss of vision is assessed by assessing the subject's best corrected visual acuity (BCVA), as is known in the art, e.g. using standard Early Treatment of Diabetic Retinopathy Study (ETDRS)-like charts). In other examples, the extent of neovascularization and/or fibrosis is assess using standard techniques such as fluorescein angiography, color fundus photography, optical coherence tomography or fundus autofluorescence.

By "isolated" is meant material that is substantially or essentially free from components that normally accompany it in its native state.

The term "ligand", as used herein, refers to any molecule which is capable of binding a receptor.

The term "local ocular administration" refers to non-systemic intraocular administration and includes, for example, intravitreal, subconjunctival, subretinal, retrobulbar and/or intracameral administration. Local ocular administration can be achieved by discrete injection, such as with a needle or other delivery device, or by implantation, such as for sustained or extended release of the active agent.

The term "non-responder to an anti-VEGF agent" refers to a subject with an ocular disease who does not, or would not, respond in the expected positive manner to therapy with an anti-VEGF agent. A non-responder therefore includes subjects who have, or would have, an incomplete response, poor response or no response to an anti-VEGF agent. Non-responders can be identified and classified according to standard criteria and definitions accepted by those skilled in the art. In some examples, a non-responder is defined as a subject exhibiting with no gain (e.g. no change or a loss (e.g. more than 0.2 or 5 letters) in best-corrected visual acuity (BVCA) after a period (e.g. 3, 6 or 12 months) of anti-VEGF treatment compared to baseline (i.e. at initiation of treatment), and/or a subject with persistent sub- or intra-retinal fluid, as detected optical coherence tomography (OCT) scan, at 3 months after initiation of anti-VEGF treatment (see e.g. Gao et al., 2020, Scientific Reports, 10:1341). In other examples, biomarkers are used to categorize a subject as a non-responder. For example, serum levels of glycerophosphocholine (GPC), lysophosphatidylcholine (LysoPC) and/or phosphatidylserine (PS) can be used to predict whether a subject is a non-responder to an anti-VEGF agent (Gao et al., 2020, Scientific Reports, 10:1341). In such examples, the subject may not have begun anti-VEGF therapy, but is categorized as a non-responder on the basis that they are predicted to not respond to anti-VEGF therapy due to their biomarker profile.

By "pharmaceutically acceptable carrier" is meant a pharmaceutical vehicle comprised of a material that is not biologically or otherwise undesirable, i.e., the material may be administered to a subject along with the selected active agent without causing any or a substantial adverse reaction. Carriers may include excipients and other additives such as diluents, detergents, coloring agents, wetting or emulsifying agents, pH buffering agents, preservatives, transfection agents and the like.

Similarly, a "pharmacologically acceptable" salt, ester, amide, prodrug or derivative of a compound as provided herein is a salt, ester, amide, prodrug or derivative that this not biologically or otherwise undesirable.

The terms "polynucleotide," "genetic material," "genetic forms," "nucleic acids" and "nucleotide sequence" include RNA, cDNA, genomic DNA, synthetic forms and mixed polymers, both sense and antisense strands, and may be chemically or biochemically modified or may contain non-natural or derivatized nucleotide bases, as will be readily appreciated by those skilled in the art.

The term "pro-inflammatory mediator" means an immunoregulatory agent that favors inflammation. Such agents include, cytokines such as chemokines, interleukins (IL), lymphokines, and tumor necrosis factor (TNF) as well as growth factors. In specific embodiments, the pro-inflammatory mediator is a "pro-inflammatory cytokine". Typically, pro-inflammatory cytokines include IL-1α, IL-1β, IL-6, and TNF-α, which are largely responsible for early responses. Other pro-inflammatory mediators include LIF, IFN-γ, IFN-β, IFN-α, OSM, CNTF, TGF-β, GM-CSF, TWEAK, IL-11, IL-12, IL-15, IL-17, IL-18, IL-19, IL-20, IL-8, IL-16, IL-22, IL-23, IL-31 and IL-32 (Tato et al., 2008. *Cell* 132:900; *Cell* 132:500, *Cell* 132:324). Pro-inflammatory mediators may act as endogenous pyrogens (IL-1, IL-6, IL-17, TNF-α), up-regulate the synthesis of secondary mediators and pro-inflammatory cytokines by both macrophages and mesenchymal cells (including fibroblasts, epithelial and endothelial cells), stimulate the production of acute phase proteins, or attract inflammatory cells. In specific embodiments, the term "pro-inflammatory cytokine" relates to TNF-α, IL-1 α, IL-6, IFNβ, IL-1β, IL-8, IL-17 and IL-18.

As used herein, the term "ocular disease or disorder" refers to a disease or disorder that affects the eye, manifesting in ocular inflammation, neovascularization and/or fibrosis, and ultimately a loss of vision. Exemplary ocular diseases or disorders that are suitable for treatment in accordance with the methods and agents of the present disclosure include wet age-related macular degeneration (wet AMD), pathological myopia, diabetic retinopathy, hereditary retinal dystrophies (also referred to as inherited retinal dystrophies (IRD), e.g. Leber's congenital amaurosis (LCA), Stargardt macular dystrophy, Best disease and Bestrophinopathies, Juvenile X-linked retinoschisis, Congenital stationary night blindness (CSNB), Achromatopsia and Usher syndrome), dry AMD, proliferative vitreoretinopathy, retinopathy of prematurity, diabetic macular oedema, neovascular glaucoma, dry eye, fibrosis associated with glaucoma filtration surgery (GFS), Coats' disease, non-infectious uveitis (NIU), macular telangiectasia (MacTel), cystoid macular edema, birdshot chorioretinopathy, Vogt-Koyanagi-Harada disease, idiopathic multifocal choroiditis, retinal vasculitis, branched vein retinal occlusions (BRVO) and central vein retinal occlusions (CRVO), polypoidal choroidal vasculopathy, Familial Exudative Vitreoretinopathy (FEVR), Idiopathic retinitis, Vasculitis, Aneurysms, and Neuroretinitis (IRVAN), Doyone honeycomb retinal dystrophy, and enhanced S-cone syndrome.

As used herein, the term "systemic administration" or "administered systemically" or "systemically administered" means introducing an agent into a subject outside of the central nervous system. As such, it is clear that local ocular administration as well as ocular implantation are not within the scope of the terms "systemic administration", "administered systemically" or "systemically administered". An agent (e.g. an antibody) or pharmaceutical composition as described herein can be systemically administered in any acceptable form such as in a tablet, liquid, capsule, powder, or the like; by intravenous, intraperitoneal, intramuscular, subcutaneous or parenteral injection; by transdermal diffusion or electrophoresis; and by minipump or other implanted extended release device or formulation. According to some embodiments, systemic administration is carried out by a route selected from the group consisting of intraperitoneal, intravenous, subcutaneous and intranasal administration, and combinations thereof.

The terms "subject", "patient" and "individual" used interchangeably herein, refer to any subject, particularly a vertebrate subject, and even more particularly a mammalian subject, (e.g. human) with a MI.

As used herein, the terms "treatment", "treating", and the like, refer to obtaining a desired pharmacologic and/or physiologic effect in a subject in need of treatment, that is, a subject who has a ocular disease or disorder. By "treatment" is meant ameliorating or preventing one or more symptoms or effects (e.g. consequences) of a ocular disease or disorder. In particular examples, treatment includes ameliorating or preventing ocular inflammation, neovascularization and/or fibrosis, and/or reducing loss of vision. Reference to "treatment", "treat" or "treating" does not necessarily mean to reverse or prevent any or all symptoms or effects of a ocular disease or disorder. For example, the subject may ultimately suffer one or more symptoms or effects, but the number and/or severity of the symptoms or effects is reduced and/or the quality of life is improved compared to prior to treatment.

Each embodiment described herein is to be applied mutatis mutandis to each and every embodiment unless specifically stated otherwise.

2. CD14 Antagonist Antibodies

The present disclosure provides methods, uses and compositions that include a CD14 antagonist antibody for treating an ocular disease or disorder in a subject. The present disclosure also provides methods, uses and compositions that include a CD14 antagonist antibody for treating an ocular disease or disorder.

The present disclosure contemplates any CD14 antagonist antibody that binds to CD14, such as human CD14 (e.g. human mCD14 or sCD14) and blocks the binding of a DAMP or PAMP to CD14 and/or that binds to CD14 and inhibits or decreases a CD14 agonist-mediated response resulting in the production of pro-inflammatory mediators, including the production of pro-inflammatory cytokines. In some embodiments, a CD14 antagonist antibody of the present invention inhibits binding of a CD14 agonist, suitably a DAMP or PAMP, to CD14 thus inhibiting or decreasing the production of pro-inflammatory cytokines. In illustrative examples of this type, the CD14 antagonist antibody is selected from the 3C10 antibody that binds an epitope comprised in at least a portion of the region from amino acid 7 to amino acid 14 of human CD14 (van Voohris et al., 1983. *J. Exp. Med.* 158: 126-145; Juan et al., 1995. *J. Biol. Chem.* 270(29): 17237-17242), the MEM-18 antibody that binds an epitope comprised in at least a portion of the region from amino acid 57 to amino acid 64 of CD14 (Bazil et al., 1986. *Eur. J. Immunol.* 16(12):1583-1589; Juan et al., 1995. *J. Biol. Chem.* 270(10): 5219-5224), the 4C1 antibody (Adachi et al., 1999. *J. Endotoxin Res.* 5: 139-146; Tasaka et al., 2003. *Am. J. Respir. Cell. Mol. Biol.*; 2003. 29(2):252-258), as well as the 28C5 and 23G4 antibodies that inhibit binding of LPS and suppress production of pro-inflammatory cytokines, and the 18E12 antibody that partly inhibits binding of LPS and suppresses production of pro-inflammatory cytokines (U.S. Pat. Nos. 5,820,858, 6,444,206 and 7,326,569 to Leturcq et al.). In some embodiments, a CD14 antagonist antibody of the present disclosure inhibits binding of CD14 to a TLR such as TLR4, thereby blocking CD14-agonist mediated response, illustrative examples of which include the F1024 antibody disclosed in International Publication WO2002/42333. Other CD14 antagonist antibodies include the single-chain antibody scFv2F9 and the related human-mouse chimeric antibody Hm2F9 (Tang et al. 2007, Immunopharmacol Immunotoxicol 29, 375-386; and Shen et al., 2014, DNA Cell Biol. 33(9): 599-604). Further examples of CD14 antagonist antibodies include the anti-human CD14 18D11 IgG1 mAb, 18D11 IgG1 F(ab)'2 fragment and the chimeric r18D11 antibody (IgG2/4) (see e.g. Lau et al., 2013, J Immunol 191:4769-4777). Each of the above references relating to CD14 antagonist antibodies is incorporated herein by reference in its entirety. The CD14 antagonist antibody may be a full-length immunoglobulin antibody or an antigen-binding fragment of an intact antibody, representative examples of which include a Fab fragment, a F(ab')2 fragment, an Fd fragment consisting of the VH and CH1 domains, an Fv fragment consisting of the VL and VH domains of a single arm of an antibody, a single domain antibody (dAb) fragment (Ward et al., 1989. *Nature* 341: 544-546), which consists of a VH domain; and an isolated CDR. Suitably, the CD14 antagonist antibody is a chimeric, humanized or human antibody.

In some embodiments, the CD14 antagonist antibody comprises a VH and VL of an antibody disclosed in U.S. Pat. No. 5,820,858:

(1) an antibody comprising:

a VL domain comprising, consisting or consisting essentially of the sequence:

```
(3C10 VL)
                                            [SEQ ID NO: 1]
QSPASLAVSLGQRATISCRASESVDSFGNSFMHWYQQKAGQPPKSSIYRA

ANLESGIPARFSGSGSRTDFTLTINPVEADDVATYFCQQSYEDPWTFGGG

TKLGNQ;
``` and a VH domain comprising, consisting or consisting essentially of the sequence:

```
(3C10 VH)
                                            [SEQ ID NO: 2]
LVKPGGSLKLSCVASGFTFSSYAMSWVRQTPEKRLEWVASISSGGTTYYP

DNVKGRFTISRDNARNILYLQMSSLRSEDTAMYYCARGYYDYHYWGQGTT

LTVSS;
```

(2) an antibody comprising:
a VL domain comprising, consisting or consisting essentially of the sequence:

(28C5 VL)
[SEQ ID NO: 3]
QSPASLAVSLGQRATISCRASESVDSYVNSFLHVVYQQKPGQPPKLLIYR

ASNLQSGIPARFSGSGSRTDFTLTINPVEADDVATYCCQQSNEDPTTFGG

GTKLEIK;

and
a VH domain comprising, consisting or consisting essentially of the sequence:

(28C5 VH)
[SEQ ID NO: 4]
LQQSGPGLVKPSQSLSLTCTVTGYSITSDSAWNWIRQFPGNRLEWMGYIS

YSGSTSYNPSLKSRISITRDTSKNQFFLQLNSVTTEDTATYYCVRGLRFA

YWGQGTLVTVSA;
and (3) an antibody comprising:
a VL domain comprising, consisting or consisting essentially of the sequence:

(18E12 VL)
[SEQ ID NO: 5]
QTPSSLSASLGDRVTISCRASQDIKNYLNWYQQPGGTVKVLIYYTSRLHS

GVPSRFSGSGSGTDYSLTISNLEQEDFATYFCQRGDTLPWTFGGGTKLEI

K;

and
a VH domain comprising, consisting or consisting essentially of the sequence:

(18E12 VH)
[SEQ ID NO: 6]
LESGPGLVAPSQSLSITCTVSGFSLTNYDISWIRQPPGKGLEWLGVIWTS

GGTNYNSAFMSRLSITKDNSESQVFLKMNGLQTDDTGIYYCVRGDGNFYL

YNFDYWGQGTTLTVSS;

Also contemplated are antibodies that comprise the VL and VH CDR sequences of the above antibodies and related antibodies, representative embodiments of which include:

(1) an antibody that comprises: a) an antibody VL domain, or antigen binding fragment thereof, comprising L-CDR1, L-CDR2 and L-CDR3, wherein: L-CDR1 comprises the sequence RASESVDSFGNSFMH [SEQ ID NO: 7] (3C10 L-CDR1); L-CDR2 comprises the sequence RAANLES [SEQ ID NO: 8] (3C10 L-CDR2); and L-CDR3 comprises the sequence QQSYEDPWT [SEQ ID NO: 9](3C10 L-CDR3); and b) an antibody VH domain, or antigen binding fragment thereof, comprising H-CDR1, H-CDR2 and H-CDR3, wherein: H-CDR1 comprises the sequence SYAMS [SEQ ID NO: 10](3C10 H-CDR1); H-CDR2 comprises the sequence SISSGGTTYYPDNVKG [SEQ ID NO: 11] (3C10 H-CDR2); and H-CDR3 comprises the sequence GYYDYHY [SEQ ID NO: 12] (3C10 H-CDR3);

(2) an antibody that comprises: a) an antibody VL domain, or antigen binding fragment thereof, comprising L-CDR1, L-CDR2 and L-CDR3, wherein: L-CDR1 comprises the sequence RASESVDSYVNSFLH [SEQ ID NO: 13] (28C5 L-CDR1); L-CDR2 comprises the sequence RASNLQS [SEQ ID NO: 14] (28C5 L-CDR2); and L-CDR3 comprises the sequence QQSNEDPTT [SEQ ID NO: 15] (28C5 L-CDR3); and b) an antibody VH domain, or antigen binding fragment thereof, comprising H-CDR1, H-CDR2 and H-CDR3, wherein: H-CDR1 comprises the sequence SDSAWN [SEQ ID NO: 16] (28C5 H-CDR1); H-CDR2 comprises the sequence YISYSGSTSYNPSLKS [SEQ ID NO: 17] (28C5 H-CDR2); and H-CDR3 comprises the sequence GLRFAY [SEQ ID NO: 18] (28C5 H-CDR3);

(3) an antibody that comprises: a) an antibody VL domain, or antigen binding fragment thereof, comprising L-CDR1, L-CDR2 and L-CDR3, wherein: L-CDR1 comprises the sequence RASESVDSYVNSFLH [SEQ ID NO: 13] (IC14 L-CDR1); L-CDR2 comprises the sequence RASNLQS [SEQ ID NO: 14] (IC14 L-CDR2); and L-CDR3 comprises the sequence QQSNEDPYT [SEQ ID NO: 27] (IC14 L-CDR3); and b) an antibody VH domain, or antigen binding fragment thereof, comprising H-CDR1, H-CDR2 and H-CDR3, wherein: H-CDR1 comprises the sequence SDSAWN [SEQ ID NO: 16] (IC14 H-CDR1); H-CDR2 comprises the sequence YISYSGSTSYNPSLKS [SEQ ID NO: 17] (IC14 H-CDR2); and H-CDR3 comprises the sequence GLRFAY [SEQ ID NO: 18] (IC14 H-CDR3); and (4) an antibody that comprises: a) an antibody VL domain, or antigen binding fragment thereof, comprising an L-CDR1, L-CDR2 and L-CDR3, wherein: L-CDR1 comprises the sequence RASQDIKNYLN [SEQ ID NO: 19] (18E12 L-CDR1); L-CDR2 comprises the sequence YTSRLHS [SEQ ID NO: 20] (18E12 L-CDR2); and L-CDR3 comprises the sequence QRGDTLPWT [SEQ ID NO: 21](18E12 L-CDR3); and b) an antibody VH domain, or antigen binding fragment thereof, comprising H-CDR1, H-CDR2 and H-CDR3, wherein: H-CDR1 comprises the sequence NYDIS [SEQ ID NO: 22](18E12 H-CDR1); H-CDR2 comprises the sequence VIWTSGGTNYNSAFMS [SEQ ID NO: 23] (18E12 H-CDR2); and H-CDR3 comprises the sequence GDGNFYLYNFDY [SEQ ID NO: 24] (18E12 H-CDR3).

In some embodiments, the CD14 antagonist antibody is humanized. In illustrative examples of this type, the humanized CD14 antagonist antibodies suitably comprise a donor CDR set corresponding to a CD14 antagonist antibody (e.g., one of the CD14 antagonist antibodies described above), and a human acceptor framework. The human acceptor framework may comprise at least one amino acid substitution relative to a human germline acceptor framework at a key residue selected from the group consisting of: a residue adjacent to a CDR; a glycosylation site residue; a rare residue; a canonical residue; a contact residue between heavy chain variable region and light chain variable region; a residue within a Vernier zone; and a residue in a region that overlaps between a Chothia-defined VH CDR1 and a Kabat-defined first heavy chain framework. Techniques for producing humanized mAbs are well known in the art (see, for example, Jones et al., 1986. *Nature* 321: 522-525; Riechmann et al. 1988. *Nature* 332:323-329; Verhoeyen et al., 1988. *Science* 239: 1534-1536; Carter et al., 1992. *Proc. Natl. Acad. Sci. USA* 89: 4285-4289; Sandhu, J S., 1992. *Crit. Rev. Biotech.* 12: 437-462, and Singer et al., 1993. *J. Immunol.* 150: 2844-2857). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al. (1991. Biotechnology 9:266-271) and Verhoeyen et al. (1988 supra). Generally, those human FR amino acid residues that differ from their murine counterparts and are located close to or touching one or more CDR amino acid residues would be candidates for substitution.

In one embodiment, the CD14 antagonist antibody is the IC14 antibody (Axtelle et al., 2001. *J. Endotoxin Res.* 7: 310-314; and U.S. Pat. Appl. No. 2006/0121574, which are incorporated herein by reference in their entireties) or an antigen-binding fragment thereof. The IC14 antibody is a chimeric (murine/human) monoclonal antibody that specifically binds to human CD14. IC14 was derived from the murine 28C5 noted above (see, U.S. Pat. Nos. 5,820,858, 6,444,206 and 7,326,569 to Leturcq et al., and Leturcq et al., 1996. *J. Clin. Invest.* 98: 1533-1538). Thus, in one example, the CD14 antagonist antibody comprises the VL domain and a VH domain, wherein:

the VL domain comprises the amino acid sequence:
[SEQ ID NO: 25]
QSPASLAVSLGQRATISCRASESVDSYVNSFLHWYQQKPGQPPKLLIYRA

SNLQSGIPARFSGSGSRTDFTLTINPVEADDVATYYCQQSNEDPYTFGGG

TKLEIK;
and the VH domain comprises the amino acid sequence:
[SEQ ID NO: 26]
LQQSGPGLVKPSQSLSLTCTVTGYSITSDSAWNWIRQFPGNRLEWMGYIS

YSGSTSYNPSLKSRISITRDTSKNQFFLQLNSVTTEDTATYYCVRGLRFA

YWGQGTLVTVSS;
or the VL domain comprises the amino acid sequence:
[SEQ ID NO: 30]
DIVLTQSPASLAVSLGQRATISCRASESVDSYVNSFLHWYQQKPGQPPKL

LIYRASNLQSGIPARFSGSGSRTDFTLTINPVEADDVATYYCQQSNEDPY

TFGGGTKLEIK;
and the VH domain comprises the amino acid sequence:
[SEQ ID NO: 31]
DVQLQQSGPGLVKPSQSLSLTCTVTGYSITSDSAWNWIRQFPGNRLEWMG

YISYSGSTSYNPSLKSRISITRDTSKNQFFLQLNSVTTEDTATYYCVRGL

RFAYWGQGTLVTVSS.

In another example, the CD14 antagonist antibody comprises light chain and heavy chain of IC14, wherein:

the light chain comprises the amino acid sequence:
[SEQ ID NO: 28]
QSPASLAVSLGQRATISCRASESVDSYVNSFLHWYQQKPGQPPKLLIYRA

SNLQSGIPARFSGSGSRTDFTLTINPVEADDVATYYCQQSNEDPYTFGGG

TKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC;
and the heavy chain comprises the amino acid sequence:
[SEQ ID NO: 29]
LQQSGPGLVKPSQSLSLTCTVTGYSITSDSAWNWIRQFPGNRLEWMGYIS

YSGSTSYNPSLKSRISITRDTSKNQFFLQLNSVTTEDTAMCVRGLRFAYW

GQGTLVTVSSASTKGPSVFPLAPCSRSTSESTAALGCLVKDYFPEPVTVS

WNSGALTSGVHTFPAVLQSSGLYSLSSVVTVPSSSLGTKTYTCNVDHKPS

NTKVDKRVESKYGPPCPSCPAPEFLGGPSVFLFPPKPKDTLMISRTPEVT

CVVVDVSQEDPEVQFNWYVDGVEVHNAKTKPREEQFNSTYRVVSVLTVLH

QDWLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYSRL

TVDKSRWQEGNVFSCSVMHEALHNHYTQKSLSLSLGK;
or the light chain comprises the amino acid sequence:
[SEQ ID NO: 32]
DIVLTQSPASLAVSLGQRATISCRASESVDSYVNSFLHWYQQKPGQPPKL

LIYRASNLQSGIPARFSGSGSRTDFTLTINPVEADDVATYYCQQSNEDPY

TFGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC;
and the heavy chain comprises the amino acid sequence:
[SEQ ID NO: 33]
DVQLQQSGPGLVKPSQSLSLTCTVTGYSITSDSAWNWIRQFPGNRLEWMG

YISYSGSTSYNPSLKSRISITRDTSKNQFFLQLNSVTTEDTATYYCVRGL

RFAYWGQGTLVTVSSASTKGPSVFPLAPCSRSTSESTAALGCLVKDYFPE

PVTVSWNSGALTSGVHTFPAVLQSSGLYSLSSVVTVPSSSLGTKTYTCNV

DHKPSNTKVDKRVESKYGPPCPSCPAPEFLGGPSVFLFPPKPKDTLMISR

TPEVTCVVVDVSQEDPEVQFNWYVDGVEVHNAKTKPREEQFNSTYRVVSV

LTVLHQDWLNGKEYKCKVSNKGLPSSIEKTISKAKGQPREPQVYTLPPSQ

EEMTKNQVSLTCLVKGFYPSDIAVEWESNGQPENNYKTTPPVLDSDGSFF

LYSRLTVDKSRWQEGNVFSCSVMHEALHNHYTQKSLSLSLGK.

Additional antagonist antibodies of CD14 suitable for use in the methods herein can be identified by methods well known to those skilled in the art. These methods generally comprise determining whether an antibody is capable of directly antagonizing CD14. For example, the methods may involve determining whether an antibody is capable of inhibiting or decreasing the amount or agonist activity of CD14, wherein the ability to inhibit or decrease the amount or agonist activity of CD14 indicates that the antibody may be suitable for use in treating MI. In some embodiments, the antibody is contacted with CD14, or a cell that expresses CD14 on its surface, or a nucleic acid sequence from which CD14 is expressed, suitably in the presence of a CD14 agonist such as a DAMP or PAMP, wherein a decrease in the amount or agonist activity of CD14 in the presence of the agonist, when compared to a control, indicates that the antibody binds to CD14 and directly antagonizes CD14. A decrease or inhibition of CD14 agonist activity, includes for example inhibiting, or decreasing activation of, downstream pathways such as TLR signaling pathways (e.g., TLR4 signaling pathway) and the TRIF pathway, or elicitation of a cellular response (e.g., production of pro-inflammatory mediators including pro-inflammatory cytokines).

These methods may be carried out in vivo, ex vivo or in vitro. In particular, the step of contacting an antibody with CD14 or with a cell that expresses CD14 on its surface (e.g., immune cells) may be carried out in vivo, ex vivo or in vitro. The methods may be carried out in a cell-based or a cell-free system. For example, the method may comprise a step of contacting a cell expressing CD14 on its surface with an antibody and determining whether the contacting of the cell with the antibody leads to a decrease in the amount or agonist activity of CD14. In such a cell-based assay, the CD14 and/or the antibody may be endogenous to the host cell, may be introduced into a host cell or tissue, may be introduced into the host cell or tissue by causing or allowing the expression of an expression construct or vector or may be introduced into the host cell by stimulating or activating expression from an endogenous gene in the cell. In such a cell-based method, the amount of activity of CD14 may be assessed in the presence or absence of an antibody in order to determine whether the agent is altering the amount of CD14 in the cell, such as through regulation of CD14 expression in the cell or through destabilization of CD14 protein within the cell, or altering the CD14 agonist activity of the cell. The presence of a lower CD14 agonist activity or a decreased amount of CD14 on the cell surface in the presence of the antibody indicates that the antibody may be a suitable antagonist of CD14 for use in accordance with the present disclosure.

In some examples, it is further determined whether the antibody lacks substantial or detectable binding to another cellular component, suitably a binding partner of CD14, such as a CD14 binding partner that is either secreted (e.g., MD2) or located on the cell membrane (e.g., TLR4), to thereby determine that the antibody is a specific antagonist of CD14. In a non-limiting example of this type, the antibody is contacted in the presence of a CD14 agonist such as a DAMP or PAMP (1) with a wild-type cell that expresses CD14 on its surface (e.g., an immune cell such as a macrophage), and (2) with a CD14 negative cell (e.g., an immune cell that is the same as in (1) but has a loss of function in the CD14 gene). If the antibody inhibits a CD14 agonist activity of the wild-type cell but not of the CD14 negative cell, this indicates that the antibody is a CD14 specific antagonist. Cells of this type may be constructed using routine procedures or animals.

In other examples, potential CD14 antagonist antibodies are assessed in vivo, such as, for example, in an animal model. In such an in vivo model, the effects of the antibody may be assessed in the circulation (e.g., blood) or heart, or in other organs such as the eye, lung, liver, kidney, or the brain. In particular examples, models of ocular diseases are used to assess the activity of the antibody (e.g. CNV laser mouse model).

Exemplary antagonist antibodies of CD14 effect a decrease in CD14 activity or levels of at least 5%, at least 10%, at least 25%, at least 50%, at least 60%, at least 75%, or at least 85% or more compared to in the absence of the antibody. In some examples, the antibody may result in a decrease in CD14 agonist activity or levels such that the agonist activity or level of CD14 is no longer detectable in the presence of the antibody. Such a decrease may be seen in the sample being tested or, for example where the method is carried out in an animal model.

Preferably, the antibody is a specific antagonist of CD14 as described above. However, this does not mean that a specific antagonist of CD14 has a complete absence of off-target antagonistic activity. In this regard, the specific antagonist of CD14 may have negligible or a minor direct binding and effect on other cellular components, such that the antagonism of the activity, signaling or expression of a non-CD14 cellular component, is less than less than 15%, less than 10%, less than 5%, less than 1%, or less than 0.1% of the direct binding and effect of that agent on the activity, signaling or expression of CD14.

Levels or amounts of CD14 may be measured by assessing expression of the CD14 gene. Gene expression may be assessed by looking at mRNA production or levels or at protein production or levels. Expression products such as mRNA and proteins may be identified or quantified by methods known in the art. Such methods may utilize hybridization to specifically identify the mRNA of interest. For example such methods may involve PCR or real-time PCR approaches. Methods to identify or quantify a protein of interest may involve the use of antibodies that bind that protein. For example, such methods may involve western blotting. Regulation of CD14 gene expression may be compared in the presence and absence of an antibody. Thus, antibodies can be identified that decrease CD14 gene expression compared to the level seen in the absence of the antibody. Such antibodies may be suitable antagonists of CD14 in accordance with the present disclosure.

The methods for identifying suitable antagonist antibodies for use in accordance with the present disclosure may assess the agonist activity of CD14. For example, such a method may be carried out using peripheral blood mononuclear cells. Such cells will produce cytokines such as IL-1 α, IL-6, TNF-α, IFN-β, IL-1β, IL-17 and IL-8 on response to stimulation with, for example, LPS. Methods may therefore comprise combining peripheral blood mononuclear cells with the antibody or a vehicle and adding LPS. The cells may then be incubated for an amount of time (e.g., 24 hours) to allow the production of pro-inflammatory mediators such as cytokines. The level of cytokines such as IL-1α, IL-6, TNF-α, IFN-β, IL-1β, IL-17 and IL-8 produced by the cells in that time period can then be assessed. If the antibody has anti-CD14 properties, then the production of such cytokines should be reduced compared to the vehicle-treated cells.

In some examples, the CD14 antagonist antibody is a multifunctional (e.g. bifunctional) antibody. In some examples, the bifunctional antibody is specific for CD14 and an inflammatory molecule and/or angiogenic molecule and/or fibrogenic molecule, such that the bifunctional antibody inhibits the activity of the inflammatory molecule and/or angiogenic and/or fibrogenic molecule. For example, the bifunctional antibody may be specific for CD14 and a complement protein (e.g. C3, C5, factor B, factor D, or properdin), angiopoietin 2 (Ang-2), VEGF or platelet-derived growth factor (PDGF).

3. Ancillary Agents and Interventions

The CD14 antagonist antibody may administered alone or in combination with other active agents (also referred to as "ancillary agents") or other interventions, such as agents and interventions useful for the treatment of an ocular disease or disorder.

Ancillary agents suitable for the purposes of the present disclosure include, for example, anti-VEGF agents, angiotensin converting enzyme (ACE) inhibitors, connective tissue growth factor (CTGF) inhibitors, complement inhibitors (including C3, C5, C5, factor B, factor D, and properdin inhibitors), angiopoietin 2 (Ang-2) inhibitors, PDGF inhibitors, statins, and steroids.

In one example, the ancillary agent is an anti-VEGF agent (or VEGF inhibitor or antagonist). VEGF is a well-characterized signal protein that stimulates angiogenesis. Anti-VEGF agents have been developed for the purposes of inhibiting angiogenesis (or neovascularization), and have become one of the few approved pharmacologic treatments for ocular diseases that are characterized by neovascularization (e.g. CNV). Anti-VEGF agents are typically administered intravitreally, although could be administered by other ocular routes, such as other local ocular routes or even topically (e.g. in the form of eye drops) with the appropriate formulation, or using extended or sustained release systems or implants. Anti-VEGF agents include, for example, anti-VEGF antibodies (e.g. brolicizumab, ranibizumab or faricimab (a bifunctional antibody that binds both VEGF and Ang-2), VEGF Trap molecules (e.g. aflibercept and conbercept), other antagonistic VEGF-binding molecules such as soluble fms-like tyrosine kinase-1 (sFlt-1 or sVEGFR-1) and antibody mimetics such as abicipar pegol (a designed ankyrin repeat protein; DARPin), and tyrosine kinase inhibitors. In some examples, the anti-VEGF agent is delivered using a vector, such as a viral vector, whereby the vector contains nucleic acid encoding the anti-VEGF agent (e.g. ADVM-022, which is an adeno-associated virus (AAV) vector encoding aflibercept; RGX-314, which is an AAV vector encoding an anti-VEGF Fab; and rAAV.sFLT-1, an AAV vector encoding sFlt-1).

In another example, administration of the antibody is in conjunction with an intervention, such as laser photocoagulation or photodynamic therapy.

When combination therapy is desired, the CD14 antagonist antibody is administered separately, simultaneously or sequentially with one or more ancillary agents or interventions. In some embodiments, this may be achieved by administering, such as systemically, a single composition or pharmacological formulation that includes both types of agent, or by administering two separate compositions or formulations at the same time, wherein one composition includes the CD14 antagonist antibody and the other the ancillary agent. In other embodiments, the treatment with the CD14 antagonist antibody may precede or follow the treatment with the ancillary agent by intervals ranging from minutes to hours or even days or weeks.

In some situations, the antibody and ancillary agent are administered within about 1-12 hours of each other or within about 2-6 hours of each other. In other situations, it may be desirable to extend the time period for treatment significantly, where one or more days (e.g. 1, 2, 3, 4, 5, 6, 7 or 8 days) or weeks (e.g. 1, 2, 3, 4, 5, 6, 7 or 8 weeks) lapse between the respective administrations. In embodiments where the ancillary agent is administered separately to the CD14 antagonist antibody, it will be understood that the ancillary agent can be administered by a method which is the same or different to that of the administration method used for the CD14 antagonist antibody.

Where two or more agents are administered to a subject "in conjunction" or "concurrently" they may be administered in a single composition at the same time, or in separate compositions at the same time, or in separate compositions separated in time.

4. Compositions

As described herein, the use of a CD14 antagonist antibody, whether alone or in combination with one or more ancillary agents, can treat an ocular disease; and/or can inhibit ocular inflammation, neovascularization and/or fibrosis in a subject with an ocular disease. The CD14 antagonist antibody and optionally the ancillary agent can be administered either by themselves or with a pharmaceutically acceptable carrier. Thus, also provided herein are compositions comprising a CD14 antagonist antibody for use in treating an ocular disease or disorder; and/or inhibiting ocular inflammation, neovascularization and/or fibrosis, in a subject with an ocular disease or disorder.

The CD14 antagonist antibodies may be formulated in a conventional manner using one or more pharmaceutically acceptable carriers, stabilizers or excipients (vehicles) to form a pharmaceutical composition as is known in the art, in particular with respect to protein active agents. Carrier(s) are "acceptable" in the sense of being compatible with the other ingredients of the composition and not deleterious to the recipient (e.g. patient) thereof. Suitable carriers typically include physiological saline or ethanol polyols such as glycerol or propylene glycol.

The antibody may be formulated as neutral or salt forms. Pharmaceutically acceptable salts include the acid addition salts (formed with free amino groups) and which are formed with inorganic acids such as hydrochloric or phosphoric acids, or such organic acids such as acetic, oxalic, tartaric and maleic. Salts formed with the free carboxyl groups may also be derived from inorganic bases such as sodium, potassium, ammonium, calcium, or ferric hydroxides, and organic bases as isopropylamine, trimethylamine, 2-ethylamino ethanol, histidine and procaine.

The compositions may be suitably formulated for systemic administration, including intravenous, intramuscular, subcutaneous, or intraperitoneal administration, local ocular administration (e.g. intravitreal, subconjunctival, subretinal, retrobulbar or intracameral administration), or topical delivery (e.g. as eye drops), and conveniently comprise sterile aqueous solutions of the antibody, which are preferably isotonic with the targeted environment in the recipient. Such formulations are typically prepared by dissolving solid active ingredient in water containing physiologically compatible substances such as sodium chloride, glycine, and the like, and having a buffered pH compatible with physiological conditions to produce an aqueous solution, and rendering said solution sterile. These may be prepared in unit or multi-dose containers, for example, sealed ampoules or vials.

The compositions may incorporate a stabilizer, such as for example polyethylene glycol, proteins, saccharides (for example trehalose), amino acids, inorganic acids and admixtures thereof. Stabilizers are used in aqueous solutions at the appropriate concentration and pH. The pH of the aqueous solution is adjusted to be within the range of 5.0-9.0, preferably within the range of 6-8. In formulating the antibody, anti-adsorption agent may be used. Other suitable excipients may typically include an antioxidant such as ascorbic acid.

The compositions may be formulated as controlled release preparations which may be achieved through the use of polymer to complex or absorb the proteins. Appropriate polymers for controlled release formulations include for example polyester, polyamino acids, polyvinyl, pyrrolidone, ethylenevinylacetate, and methylcellulose. Another possible method for controlled release is to incorporate the antibody into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions. Thus, in particular examples, the CD14 antagonist antibody and optionally an ancillary agent are formulated for sustained or extended release, such as in non-biodegradable implants (e.g. the Posterior Micropump™ (PMP) drug delivery system by Replenish, Inc. (Humayun et al. 2014, Transl Vis Sci Technol. 3(6):5), and the port delivery system (PDS) by Genentech (Campochiaro et al. 2019, Opthamology, 126:1141-1154), biodegradable implants, nanoformulations (including nanoparticuales, microparticles, liposomes and dendrimers) and hydrogels (see e.g. Seah et al., 2020, Eye, 34:1341-1356). In some examples, where the composition is formulated for topical administration to the eye (e.g. as eye drops), the composition contains cell-penetrating peptides (CPPs) to assist in penetration of the CD14 antagonist antibody across tissue barriers, both into cells and between cells (see e.g. Cogan et al., 2017, Investigative Ophthalmology & Visual Science, 58:2578-2590). Modes and compositions for delivery of therapeutic antibodies to the eye are well known in the art and any one can be used for administration of a CD14 antagonist antibody in accordance with the present disclosure (Mandel et al., 2018, Adv Drug Deliv Rev. 126: 67-95).

A CD14 antagonist antibody and optionally an ancillary agent may also be administered directly to the airways in the form of an aerosol. For use as aerosols, the inhibitors of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

One of skill in the art will recognize that formulations are routinely designed according to their intended use, i.e. route of administration.

5. Methods of Treatment

The present disclosure provides for therapeutic methods for treating a subject with an ocular disease or disorder, such as an ocular disease or disorder that is characterized by ocular inflammation, neovascularization and/or fibrosis (i.e. ocular inflammation, neovascularization and/or fibrosis is typically observed in patients with the ocular disease or disorder). In particular examples, the ocular disease or disorder is characterized by the presence or development of fibrosis, and treatment of the subject prevents, inhibits or ameliorates fibrosis.

Exemplary ocular diseases or disorders include, but are not limited to, pathological myopia, AMD (including wet and dry AMD), diabetic retinopathy, hereditary retinal dystrophies, proliferative vitreoretinopathy, retinopathy of prematurity, diabetic macular oedema, neovascular glaucoma, dry eye, fibrosis associated with glaucoma filtration surgery (GFS), Coats' disease, non-infectious uveitis (NIU), macular telangiectasia (MacTel), cystoid macular edema, birdshot chorioretinopathy, Vogt-Koyanagi-Harada disease, idiopathic multifocal choroiditis, retinal vasculitis, branched vein retinal occlusions (BRVO) and central vein retinal occlusions (CRVO), polypoidal choroidal vasculopathy, Familial Exudative Vitreoretinopathy (FEVR), Idiopathic retinitis, Vasculitis, Aneurysms, and Neuroretinitis (IRVAN), Doyone honeycomb retinal dystrophy, and enhanced S-cone syndrome. Such ocular diseases or disorders are characterized by ocular (e.g. retinal, subretinal, epiretinal, choroidal, corneal, optical nerve, macula, etc.) inflammation, neovascularization and/or fibrosis. Consequently, administration of a CD14 antagonist antibody, which is demonstrated herein to inhibit both neovascularization and fibrosis and is a known anti-inflammatory agent, can have particular therapeutic benefits. Typically, the subject is diagnosed with the ocular disease or disorder prior to application of the methods of the present disclosure, such as by a medical practitioner on the basis of accepted criteria known to those practitioners and widely used in the art.

In one example, the ocular disease or disorder is pathological myopia (also known as high myopia or degenerative myopia). Pathological myopia is a form of severe and progressive nearsightedness characterized by changes in the fundus of the eye, due to posterior staphyloma and deficient corrected acuity, and is commonly defined as having a spherical equivalent ≤−6.0 D, or axial length ≥26.5 mm (Shih et al., 2006, Br J Ophthalmol 90: 546-550). Clinically, the funduscopic changes associated with pathological myopia include straightened and stretched vessels, temporal peripapillary atrophic crescent, tilting of the optic disc, posterior staphyloma, lacquer cracks in the Bruch's membrane, subretinal haemorrhage and CNV, which is associated with a significant reduction in corrected vision. Thus, in some embodiments, the subject with pathological myopia has CNV. Pathological myopia is also characterized by the development of ocular fibrosis, including after treatment with anti-VEGF agents (see e.g., Ahn et al., 2016, Retina, 36(11):2140-2149; Xiao et al., 2020, Br J Ophthalmol; and Zhu et al. 2016. Cochrane Database of Systematic Reviews. Issue 12. Art. No.: CD011160).

In a further example, the ocular disease is AMD, which is characterized by neovascularisation causing vision distortion and thickening of the Bruch's membrane. In one embodiment, the AMD is dry AMD. Dry AMD is characterized by the accumulation of small drusen in the retinal pigment epithelium (RPE) leading to a loss of RPE and to a degeneration of the retina in the macular region. In some instances, the dry AMD is early dry AMD. In other instances, the dry AMD is late dry AMD without geographic atrophy. In other examples, the AMD is wet AMD. Wet AMD is usually preceded by dry AMD and is characterized by neovascular membranes derived from the choroidal vasculature that invade Bruch's membrane, leak, and often cause detachments of the RPE and or the neural retina. These new capillaries are abnormally permeable, allowing accumulation of serum and blood under the RPE and or the neurosensory retina. The leaking blood vessels generally lead to a scarring of the macula. The loss of vision in patients with wet AMD can be rapid and result in functional blindness. In patients with wet AMD the complex formed by the choroidal new vessels and the fibrous tissue can destroy the photoreceptors relatively rapidly, e.g. within 3-24 months.

In another example, the ocular disease is diabetic retinopathy. Diabetic retinopathy is an ocular complication of diabetes, characterized by microaneurysms, hard exudates, hemorrhages, and venous abnormalities in the non-proliferative form and neovascularization, preretinal or vitreous hemorrhages, and fibrovascular proliferation in the proliferative form. Hyperglycemia induces these microvascular retinal changes, leading to blurred vision, dark spots or flashing lights, and sudden loss of vision. Like pathological myopia and AMD, diabetic retinopathy is characterized by ocular inflammation, neovascularization and fibrosis (see e.g. Roy et al., 2016, Experimental Eye Research 142: 71e75; Murakami et al., 2020, Progress in Retinal and Eye Research 74:100778).

In other examples, the ocular disease is hereditary retinal dystrophy, proliferative vitreoretinopathy, retinopathy of prematurity, diabetic macular oedema, neovascular glaucoma, dry eye, fibrosis associated with GFS, Coats' disease, non-infectious uveitis, macular telangiectasia, cystoid macular edema, birdshot chorioretinopathy, Vogt-Koyanagi-Harada disease, idiopathic multifocal choroiditis, retinal vasculitis, branched vein retinal occlusions and central vein retinal occlusions, polypoidal choroidal vasculopathy, FEVR, IRVAN, Doyone honeycomb retinal dystrophy, or enhanced S-cone syndrome, each of which are also characterized by ocular inflammation, neovascularization and/or fibrosis (see e.g. Idrees et al., 2019, Int Ophthalmol Clin. 59(1): 221-240, Enriquez et al. 2020, Asia-Pacific Journal of Ophthalmology 9(4):358-368; Cetin et al. 2018, Graefe's Archive for Clinical and Experimental Ophthalmology, 256: 1801-1806, Marano et al. 2000, Graefe's Arch Clin Exp Ophthalmol, 238:760-764; Sen et al., 2019, Indian J Ophthalmol. 67(6): 763-771; Schlunck et al. 2016, Exp. Eye Res. 142, 76-82; Zhavoronkov et al., 2016, Cell Cycle 15(15): 2087; Golzarri et al., 2020, Ocul Immunol Inflamm October 6; 1-5; Khojasteh et al., 2021, J Ophthalmol April 30:6674290; Alsalamah et al., 2021, Ophthalmol Retina 5(9):918-927; Tarib et al., 2020, J Clin Exp Ophthal, 11(1): 1000824).

Contemplated herein are therefore methods for treating an ocular disease, such as an ocular disease associated with or characterized by ocular inflammation, neovascularization and/or fibrosis (e.g. pathological myopia, AMD (including wet and dry AMD), diabetic retinopathy, hereditary retinal dystrophies, proliferative vitreoretinopathy, retinopathy of prematurity, diabetic macular oedema, neovascular glaucoma, dry eye, fibrosis associated with GFS, Coats' disease, non-infectious uveitis, macular telangiectasia, cystoid macular edema, birdshot chorioretinopathy, Vogt-Koyanagi-Harada disease, idiopathic multifocal choroiditis, retinal vasculitis, branched vein retinal occlusions and central vein retinal occlusions, polypoidal choroidal vasculopathy, FEVR, IRVAN, Doyone honeycomb retinal dystrophy, or enhanced S-cone syndrome), in a subject by administering to the subject a CD14 antagonist antibody, and optionally administering an ancillary agent or performing an intervention, and methods for inhibiting ocular inflammation, neovascularization and/or fibrosis in a subject with an ocular disease (e.g. pathological myopia, AMD (including wet and dry AMD), diabetic retinopathy, hereditary retinal dystrophies, proliferative vitreoretinopathy, retinopathy of prematurity, diabetic macular oedema, neovascular glaucoma, fibrosis associated with GFS, Coats' disease, non-infectious uveitis, macular telangiectasia, cystoid macular edema, birdshot chorioretinopathy, Vogt-Koyanagi-Harada disease, idiopathic multifocal choroiditis, retinal vasculitis, branched vein retinal occlusions and central vein retinal occlusions, polypoidal choroidal vasculopathy, FEVR, IRVAN, Doyone honeycomb retinal dystrophy, or enhanced S-cone syndrome) by administering to the subject a CD14 antagonist antibody, and optionally administering an ancillary agent or performing an intervention. Where the method is for treating fibrosis associated with GFS, the subject has had GFS. Thus, provided are methods for inhibiting ocular inflammation, neovascularization and/or fibrosis in a subject that has had GFS. In some instances, the subject is administered the CD14 antagonist antibody 1, 2, 3, 4, 5, 6 or more hours, 1, 2, 3, 4, 5, 6 or more days, and/or 1, 2, 3, 4, 5, 6 or more weeks, after the subject has had GFS.

The CD14 antagonist antibody, and optionally the ancillary agent (collectively referred to herein as "therapeutic agents"), will be administered in an "effective amount(s)", to achieve an intended purpose in a subject, such as the reduction or prevention of one or more symptoms or consequences of the ocular disease, e.g. the inhibition or amelioration of ocular inflammation, neovascularization and/or fibrosis, inhibition of the development of lesions, and/or inhibition or slowing of loss of vision. The dose of therapeutic agents(s) administered to a patient should be sufficient to achieve a beneficial response in the subject. In some examples, the administration of the antibody (optionally with an ancillary agent) results in the inhibition or amelioration of ocular inflammation, neovascularization and/or fibrosis compared to when the antibody is not administered. In other examples, the administration of the antibody (optionally with an ancillary agent) results in a reduction, inhibition or a slowing of a loss of vision compared to when the antibody is not administered.

In particular examples, the subject with the ocular disease has, or is at risk of developing, ocular fibrosis (e.g. retinal, subretinal or epiretinal fibrosis, including epiretinal membrane (ERM). Thus, in some embodiments, subjects that have, or are at risk of developing, ocular fibrosis are identified or selected for treatment in accordance with the methods of the present disclosure.

For example, in some embodiments, the subject has received an anti-VEGF therapy for at least 3, 6, 12, 14, 16 or 18 months. As has been previously described, patients with ocular disease (e.g. AMD, pathological myopia (e.g. with CNV), diabetic retinopathy, retinopathy of prematurity, etc.) that are being treated with an anti-VEGF therapy can develop ocular fibrosis (see Daniel et al., 2018, Ophthalmology 125(7): 1037-1046; Ahn et al., 2016, Retina, 36(11): 2140-2149; Xiao et al., 2020, Br J Ophthalmol., Osaadon, 2014, Eye (Lond), 28(5): 510-520; Li et al., 2015, Int J Ophthalmol. 8(6): 1202-1206; Hu et al., 2017, Journal of Ophthalmology, Article ID 5078565; Tong et al., BMC Ophthalmology, 18:150), which itself can be associated with accelerated loss of vision. Accordingly, in some embodiments the present disclosure provides methods for treating an ocular disease in a subject by administering to the subject a CD14 antagonist antibody, and optionally administering an ancillary agent or performing an intervention, wherein the subject has received an anti-VEGF therapy for at least 3, 6, 12, 14, 16 or 18 months. The present disclosure also provides methods for inhibiting ocular fibrosis in a subject with an ocular disease, by administering to the subject a CD14 antagonist antibody, and optionally administering an ancillary agent or performing an intervention, wherein the subject has received an anti-VEGF therapy for at least 12, 14, 16 or 18 months. In these embodiments, the subject may have received regular (i.e. at defined or pre-therapy intervals, such as monthly) anti-VEGF therapy, or intermittent (e.g. "as needed") anti-VEGF treatment as determined by a medical practitioner.

In further examples, the present disclosure provides methods for treating an ocular disease in a subject by administering to the subject a CD14 antagonist antibody, and optionally administering an ancillary agent or performing an intervention, wherein the subject has received a treatment for ocular neovascularization (including CNV) for at least 3, 6, 12, 14, 16 or 18 months. Treatment for neovascularization may include, in additions to anti-VEGF agents, tyrosine kinase inhibitors such as Tie2 inhibitors, and Ang-2 inhibitors. The present disclosure also provides methods for inhibiting ocular fibrosis, neovascularization and/or inflammation in a subject with an ocular disease, by administering to the subject a CD14 antagonist antibody and optionally administering an ancillary agent or performing an intervention, wherein the subject has received a treatment for ocular neovascularization for at least 3, 6, 12, 14, 16 or 18 months. In these embodiments, the subject may have received regular (i.e. at defined or pre-determined intervals, such as monthly) treatment for ocular neovascularization, or intermittent treatment for ocular neovascularization as determined by a medical practitioner (e.g. "as needed").

Evidence of ocular fibrosis in a subject with ocular disease can also be used to identify or select a patient population for treatment with a CD14 antagonist antibody in accordance with the present disclosure. For example, hyper-reflective material (HRM) as observed by optical coherence tomography (OCT) is considered a biomarker of fibrosis (see e.g. Casalino et al. Exp Rev Opthamology 15(2):83-91). In other examples, the presence of fibrotic lesions (or scars) is detected by, for example, fluorescein angiography, color fundus photographs (CFP) or fundus autofluorescence (FAF) imaging, as is known to those skilled in the art (see e.g. Daniel et al., 2014, Ophthalmology, 121(3): 656-666).

In further examples, the subject with an ocular disease is selected for treatment with an anti-CD14 antagonist antibody on the basis that they are non-responders to treatment with an anti-VEGF agent. Accordingly, in some embodiments the present disclosure provides methods for treating an ocular disease in a subject by administering to the subject a CD14 antagonist antibody, and optionally administering an ancillary agent or performing an intervention, wherein the subject is a non-responder to treatment with anti-VEGF agent. The present disclosure also provides methods for inhibiting ocular inflammation, neovascularization and/or fibrosis in a subject with an ocular disease, by administering to the subject a CD14 antagonist antibody, and optionally administering an ancillary agent or performing an intervention, wherein the subject is a non-responder to treatment with an anti-VEGF agent. Subjects can be categorized as non-responders to anti-VEGF therapy using standard criteria known to those skilled in the art. For example, a subject may be categorized a non-responder if they exhibit no gain (e.g. no change or a loss (e.g. of more than 0.2 or 5 letters) in BVCA after a period (e.g. 3, 6 or 12 months) of anti-VEGF therapy. In other examples, biomarkers are used to categorize a subject as a non-responder.

The quantity or dose frequency of the therapeutic agent(s) to be administered may depend on the subject to be treated, inclusive of their diagnosis (e.g. the type of ocular disease or the type or severity symptoms they present with), age, sex, weight and general health condition thereof. In this regard, precise amounts of the therapeutic agent(s) for administration will depend on the judgment of the practitioner. One skilled in the art would be able, by routine experimentation, to determine an effective, non-toxic amount of a CD14 antagonist antibody, and optionally an ancillary agent described herein, for administration to a subject. In particular examples, the amount of CD14 antagonist antibody administered to a subject is between 0.1 mg/kg and 50 mg/kg, between 0.5 mg/kg and 40 mg/kg, between 2 mg/kg and 20 mg/kg or between 5 mg/kg and 10 mg/kg. In particular examples, the amount of CD14 antagonist antibody administered to a subject is (or is about) 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg/kg.

The CD14 antagonist antibody may be administered to the subject as a single dose or multiple doses. In particular embodiments, the CD14 antagonist antibody is administered as multiple doses. In embodiments where the CD14 antagonist antibody is administered as multiple doses, doses may be administered as regular or semi-regular doses (e.g. monthly), or "as-needed", as determined by a medical practitioner. In some examples, the CD14 antagonist antibody is administered every 2, 3, 4, 5, 6, 7, 8, 9, 10, 11 or 12 weeks, and for a duration of 2, 3, 4, 5, 6, 7, 8, 9, 10, 11, 12, 24, 48 or more months or 3, 4, 5, 6, 7, 8, 9 10 or more years.

Administration may be any route suitable, including local ocular administration (e.g. intravitreal, subconjunctival, subretinal, retrobulbar or intracameral administration, including discrete injection or implantation), topical administration (e.g. by eye drops) or systemic administration.

In order that the invention may be readily understood and put into practical effect, particular preferred embodiments will now be described by way of the following non-limiting example.

EXAMPLES

Example 1

Assessment of the Effect of Anti-CD14 Treatment on CNV

A study was performed to evaluate the effect of an anti-CD14 antagonist antibody in a laser-induced mouse model of choroidal neovascularization (CNV). The active agent used in the study was the biG53 F(Ab')2 antibody, which functionally inhibits PAMP-dependent cytokine production in a dose dependent manner similar to that observed with the anti-human CD14 mAb IC14 (International patent application no. PCT/US2020/043619). The effect of this CD14 antagonist was compared to aflibercept (VEGF Trap-eye).

A. Materials and Methods

Laser Induced Choroidal Neovascularization

The laser induced mouse model of CNV is a well-established model for evaluating ocular diseases such as wet AMD. Briefly, mice were deeply anaesthetized by an intraperitoneal (IP) injection of a combination of ketamine (60 mg/kg; Provet, Heatherton, VIC, Australia) and xylazine (13 mg/kg; Troy Laboratories, Glendenning, NSW, Australia) and their eyes further anaesthetized with 0.5% proparacaine hydrochloride (Alcaine; Alcon Laboratories, Frenchs Forest, NSW, Australia). Pupils were dilated by topical application of 1% atropine sulfate (Alcon Laboratories) and 2.5% phenylephrine hydrochloride (Bausch & Lomb, Chatswood, NSW, Australia). Each animal had four laser burns applied to each eye using an image guided (Micron IV, Phoenix Research Laboratories, Pleasanton, Calif., USA) argon laser (532 nm diode, 350 mW, 70 ms pulse duration). Immediately after laser treatment a fundus image was collected, and ocular treatment applied as detailed below.

Intravitreal Injection (IV) of Agents

Treatment concentrations and injections of various agents were as follows:

1 µl aliquot of anti-CD14 at 740 µg/ml 1.5 and 2 µl aflibercept (15 µg/µl, 60 µg/µl, 80 µg/µl per eye), prepared by diluting human aflibercept (40 mg/ml) to the appropriate concentration.

1.5 µl anti-VEGF164 neutralizing antibody (200 ng/µl; AF493-NA, R&D Systems)

1 µl PBS

Injections were applied to left and right eyes using a custom Hamilton syringe attached to a sterile 31 g needle. Following intravitreal injection, animals were allowed to recover and placed in their boxes for 7 days. A second cohort of animals received 1 µl anti-CD14 or PBS and 2 µl aflibercept (80 µg/µl per eye) seven days after laser treatment and then underwent experimentation at day 14.

Fluorescein Angiography and Tissue Collection 7 days or 14 days after laser treatment animals were anaesthetized with a combination of xylazine and ketamine and fundus fluorescein angiography was performed on both eyes using a Micron IV retinal camera (Phoenix Research Laboratories, Pleasanton, Calif., USA). Images were collected for each eye immediately after injection of 1% sodium fluorescein and then 5 and 10 minutes after injection. Following imaging, animals were killed by cervical dislocation, their eyes were removed and placed in either: (a) fixative containing 60% Ethanol, 5% acetic acid, 4% paraformaldehyde, 3% sucrose in distilled water and fixed overnight or (b) the retina and RPE were separated and placed in RLT buffer for RNA analysis.

Analysis of Lesion Size

Following fluorescein angiography, each tiff file was extracted, and the area of each lesion was quantified using a semi-automated macro in Image J (a Java-based image processing program developed at the National Institutes of Health and the Laboratory for Optical and Computational Instrumentation. A set of criteria was used for this analysis where all laser spots with hemorrhage as well as fused lesions were excluded from analysis.

Quantification of Lesion Height and Fibrosis

Following sectioning of eye cups, slides were labelled with Masson's trichrome stain and digital images of each lesion were captured. Lesion size is quantified by measuring the height of the lesion normalizing to the thickness of the choroid. For each sample, three sections were analysed and averaged to obtain a single value.

Total RNA Extraction and Quantitative Real-Time PCR

Quantification of angiogenic and fibrosis gene expression was performed as previously described (Jobling et al. 2015, FASEB J 29(2): 696-710). Total RNA was isolated from frozen RPE/choroidal complexes after 7 and 14 days of CNV using commercial spin columns (RNeasy® Micro Kit, Qiagen) incorporating an on-column DNase I digest to remove genomic contamination. Unlasered tissues from aged matched control mice were used as controls. RNA concentration and quality were assessed the Agilent 2200 Tape Station (Agilent Technologies 5067-5583 D1000, Germany) according to manufacturer's instructions. Samples with RNA integrity number (RIN) above 8 were used for quantitative PCR.

For standard real time qPCR, reverse transcription reactions were performed on 75 ng total RNA using random hexamer primers (Omni script, Qiagen) and subsequently diluted to ~3 ng/µl. Expression of several genes related to CNV/fibrosis were assessed relative to the housekeeping genes, hypoxanthine guanine phophoribosyl transferase (Hprt) and glyceraldehyde -3-phosphate dehydrogenase (Gapdh). External standards were produced using the same primer pairs that incorporated T7 promoter and polyT15 sequences at the 5' end of each forward and reverse primer, respectively. The amplified standards were transcribed into copy RNA (Megascript T7 High Yield Transcription kit; Ambion Inc., Austin, Tex.) and dilutions combined with yeast t-RNA (75 ng; Invitrogen, Carlsbad, Calif.) to reflect the retinal total RNA amount (75 ng) used in the reverse transcription reaction. The RNA standards were reverse transcribed with the retinal RNA samples to standardise efficiency.

Real-time PCR was performed on the Rotorgene V3000 (Corbett Research, Australia) using a commercial reaction mixture incorporating SYBR green (SensiFast, Bioline). Respective four-point standard curves were included in every run and standards and samples were amplified in triplicate. Absolute gene copy number was calculated with reference to the standard curve (Rotorgene V6.1 software, Australia) and expressed relative to Hprt and Gapdh.

To analyse global changes in gene expression, Fibrosis RT$^2$ Profiler™ PCR Array (Cat #: PAMM-12ZE; Qiagen, Australia) was used. RNA samples from each experimental group were pooled (n=9 for each experimental group and n=3 pooled samples). 75 ng of total RNA was amplified, and reverse transcribed into complementary DNA (cDNA) using RT2 PreAMP cDNA Synthesis Kit (Qiagen, VIC, Australia) according to the manufacturer's instructions (RT2 PreAMP cDNA Synthesis Handbook; Qiagen). Subsequently, RT2 SYBR Green Mastermix (Qiagen) was mixed with each cDNA sample and then added across the 384-well plate containing 4 replicates of 96-well assays including 84 fibrosis-related (Table 1), genes, 5 housekeeper control genes, 1 genomic DNA control, 3 reverse transcription controls and 3 positive PCR control.

TABLE 1

Fibrosis-associated genes in PCR array

| Type of gene | Gene |
|---|---|
| Pro-Fibrotic: | Acta2 (α-SMA), Agt, Ccl11 (eotaxin), Ccl12 (MCP-5, Scya12), Ccl3 (Mip-1a), Ctgf, Grem1, Il13, Il13ra2, Il4, Il5, Snai1 (Snail). |
| Anti-Fibrotic: | Bmp7, Hgf, Ifng, Il10, Il13ra2. |
| Extracellular Matrix (ECM) Structural Constituents: | Coi1a2, Col3a1. |
| Extracellular Matrix (ECM) Remodeling Enzymes: | Lox, Mmp1a, Mmp13, Mmp14, Mmp2, Mmp3, Mmp8, Mmp9, Plat (tPA), Plau (uPA), Pig, Serpina1, Serpine1 (PAI-1), Serpinh1 (Hsp47), Timp1, Timp2, Timp3, Timp4. |
| Cell Adhesion Molecules: | Itga1, Itga2, Itga3, Itgav, Itgb1, Itgb3, Itgb5, Itgb6, Itgb8. |

TABLE 1-continued

Fibrosis-associated genes in PCR array

| Type of gene | Gene |
| --- | --- |
| Inflammatory Cytokines & Chemokines: | Ccl11 (eotaxin), Ccl12 (MCP-5, Scya12), Ccl3 (Mip-1a), Ccr2, Cxcr4, Ifng, Il10, Il13, Il13ra2, Il1a, Il1b Il4, Il5, Ilk, Tnf. |
| Growth Factors: | Agt, Ctgf, Edn1, Egf, Hgf, Pdgfa, Pdgfb, Vegfa. |
| TGFβ Superfamily Members: | Bmp7, Cav1, Dcn, Eng (Evi-1), Grem1, Inhbe, Ltbp1, Smad2 (Madh2), Smad3 (Madh3), Smad4 (Madh4), Smad6, Smad7, Tgfb1, Tgfb2, Tgfb3, Tgfbr1 (ALK5), Tgfbr2, Tgif1, Thbs1 (TSP-1), Thbs2. |
| Transcription Factors: | Cebpb, Jun, Myc, Nfkb1, Sp1, Stat1, Stat6. |
| Epithelial-to-Mesenchymal Transition (EMT): | Akt1, Bmp7, Col1a2, Col3a1, Itgav, Itgb1, Mmp2, Mmp3, Mmp9, Serpine1 (PAI-1), Smad2 (Madh2), Snai1 (Snail), Tgfb1, Tgfb2, Tgfb3, Timp1. |
| Other Fibrosis Genes: | Bcl2, Fasl (Tnfsf6). |

The cDNA was amplified using the Applied Biosystems ViiA 7 Real-Time PCR System (Thermo Fisher Scientific, Wilmington, Del., USA) at 95° C. for 15 min., followed by 95° C. for 15 seconds and 60° C. for 1 min. (40 cycles). To obtain statistically valid data, three independent arrays were run for each experimental group. The data were analyzed using Gene Global RT2 Profiler PCR Data Analysis tool from QIAGEN website.

Quantification of VEGF Protein Expression

At 2, 7, and 14 days after laser treatment, eyes were enucleated, retina and RPE/choroid isolated and immediately snap frozen in liquid nitrogen. To prepare tissue homogenates, samples were placed in 250 ul of 1×PBS with added 1% Protease inhibitor cocktail (P8340, Sigma) and sonicated for 5 minutes on ice. After performing three freeze-thaw cycles to break the cell membranes, the homogenates were placed on ice for 30 minutes, centrifuged at 14,000 rpm for 10 minutes at 4° C. and supernatants were collected. Total protein concentration was quantified using Pierce™ BCA Protein Assay Kit (ThermoFisher scientific, Australia). VEGF levels were analysed by a commercially available ELISA kit (Quantikine; R&D Systems) according to the manufacturer's instructions. The VEGF concentration (pg/ml) in each sample was calculated from the standard curve and normalized to total protein concentration (pg/mg of total protein). For each sample, tissues from both eyes were pooled to obtain sufficient protein.

Analysis of Innate Immune Cell Migration by Flow Cytometry

Laser-treated eyes were enucleated at day 2 and 7 and RPE/choroid harvested from both eyes. The isolated RPE/choroid was cut in small pieces, incubated in 500 μl of digestion cocktail (0.1 mg/ml Liberase TL and 0.2 mg/ml DNase1) at 37° C. for 60 minutes with mechanical dissociation at time 20, 40, and 60 minutes. Cells were filtered through 40 um nylon strainer, spun at 350 g for 10 minutes and washed twice in FACS buffer containing 1% BSA and 0.1% sodium azide. Cells were incubated with Fc-Block (553142, BD Biosciences) for 15 minutes, washed twice and stained with titrated concentrations of fluorochrome-conjugated antibodies for 30 minutes. Spleen tissue was used as a positive control for each run. Antibodies utilised are provided in Table 2.

Briefly, cells were gated based on CD45 expression to identify leucocytes (CD45+/CD34−), and then separated based on CD11b, CD11c expression (dendritic cells and other myeloid cells) and Ly6C and Ly6G to identify inflammatory monocytes, resident monocytes/macrophages and neutrophils. The proportions of different subpopulations of leucocytes were quantified in unlasered (non-CNV), vehicle, aflibercept (80 μg/μl), and anti-CD14 treated eyes.

TABLE 2

Antibodies used in flow cytometry.

| Antibody | Target cell type | Supplier |
| --- | --- | --- |
| ViaKrome 808 | Live/dead cells | Beckman Coulter |
| CD45 | Leukocytes | BD Biosciences |
| CD11b | Myeloid cells | BD Biosciences |
| CD11c | Dendritic cell | Biolegend |
| Ly6C | Monocytes | Biolegend |
| Ly6G | Neutrophils | Biolegend |
| CD14 | Monocytes/Macrophages | Biolegend |
| MHCII | Dendritic cell Circulating fibrocytes | Biolegend |
| CCR2 | Monocytes/macrophages Circulating fibrocytes | Biolegend |
| CD34 | Fibrocytes | Biolegend |

B. Results

Effect of Treatment on Lesion Size

The size of lesions induced by laser injury is considered a surrogate measure of angiogenesis that is associated with choroidal neovascularization (CNV). The effect that different concentrations of aflibercept or a mouse neutralizing antibody targeting VEGF had in reducing lesion size 7 days after laser induced CNV was assessed. As shown in FIG. 1A, treatment with aflibercept reduced the size of laser induced lesions, but only when the dose injected was ~20 times higher than what is conventionally used in the treatment of human wet AMD. In comparison to PBS (vehicle injection), high dose aflibercept (80 μg/μl) significantly reduced the size of lesions 7 days following laser induced CNV (One-way ANOVA, post-hoc Tukey's test, p<0.001; vehicle vs aflibercept p=0.0048). Fluorescein angiography lesion size following treatment with aflibercept (15 μg/μl, 60 μg/μl) and also anti-VEGF164 (300 ng/ul) was also compared and no change from vehicle was found (One-way ANOVA, post-hoc Tukey's test).

To put this result in greater context of human disease—those with wet AMD are treated with an 50 μl injection of 40 mg/ml aflibercept into the human vitreous which has a volume of 4.4 ml. This equates to a vitreal concentration of aflibercept of 0.45 mg/ml (or 0.45 μg/μl). 15 μg/μl, 60 μg/μl and 80 μg/μl was injected into the mouse eye, which has a vitreal volume of 8 μl. This equates to vitreal concentrations of aflibercept 1.875 μg/μl, 7.5 μg/μl and 10 μg/μl, all far higher than used for treating human disease.

The efficacy of CD14 treatment with vehicle and high dose aflibercept (80 μg/μl) was then compared. As shown in FIG. 1B, anti-CD14 was as effective in reducing laser induced lesion size as high dose aflibercept. Notably, anti-CD14 reduced lesion size by (~34%+4%) which was similar to the effect induced by high dose aflibercept (~32%+8%).

Effect of Treatment on Fibrosis

Figure 2:
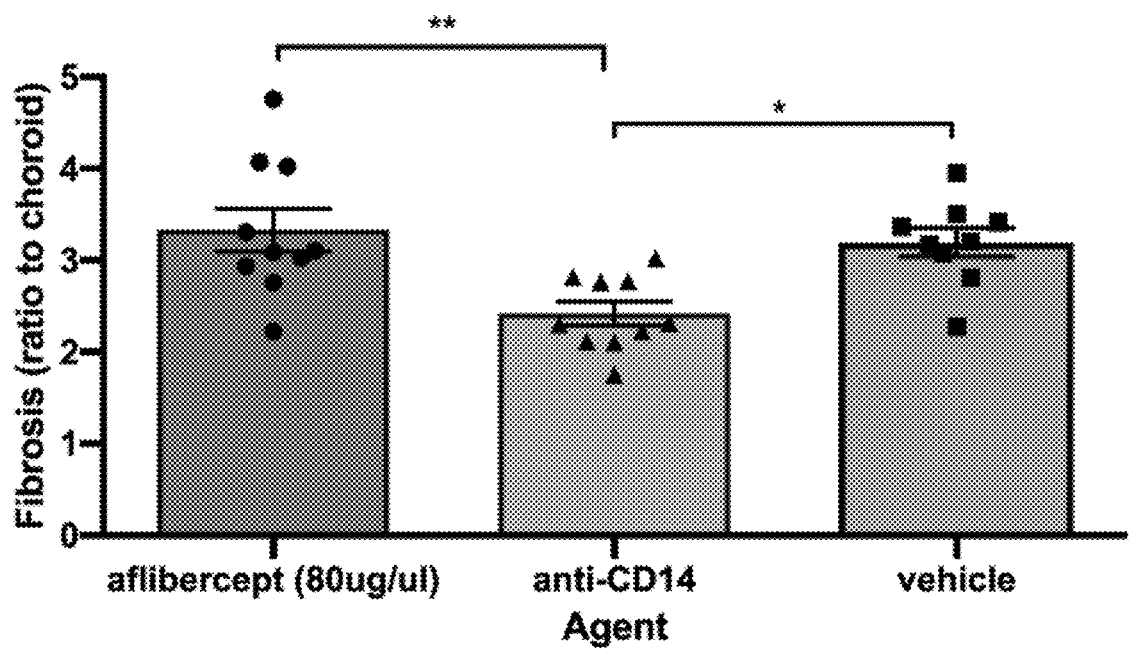
FIG. 2 is a graphical representation of fibrosis 7 days after laser induced choroidal neovascularization. Graph of mean+SEM ratio of fibrosis in vehicle and anti-CD14 treated eyes evaluated at day 7. One-way ANOVA, post-hoc Tukey's test, *$p<0.05$; ** $p<0.01$, n≥8.
Figure 3:
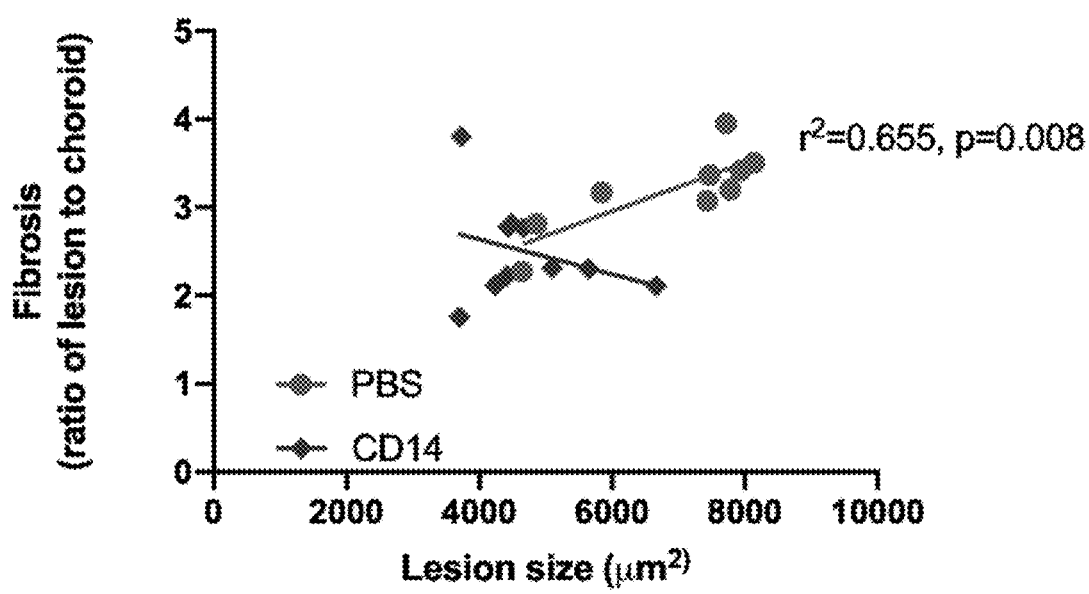
FIG. 3 is a graphical representation of the correlation between fibrosis and angiogenesis in eyes treated with anti-CD14 and vehicle 7 days after laser induced choroidal neovascularization.

In order to assess the development of fibrosis following laser induced CNV, a Masson's trichrome stain was used as a means of labeling collagen, and then the height of the laser induced lesion relative to an adjacent area of choroid was quantified. Anti-CD14, vehicle, three concentrations of aflibercept and anti-VEGF164 on fibrosis 7 days after laser induced CNV was compared. As shown in FIG. 2, anti-CD14 significantly reduced fibrosis when compared to the vehicle treatment and high dose aflibercept (One way ANOVA, posthoc Tukeys test; anti-CD14 vs vehicle, p=0.015; anti-CD14 vs aflibercept, p=0.0034; aflibercept vs vehicle p=0.86). The correlation between laser induced lesion size and development of fibrosis following each of the treatments was then assessed (FIG. 3). As expected, there was a positive correlation between increasing lesion size and increasing fibrosis in eyes treated with a vehicle (PBS; Pearson's correlation). In contrast, treatment with anti-CD14 showed no correlation, wherein irrespective of lesion size (i.e. angiogenesis), development of fibrosis was uniform.

Quantification of Gene Expression in Eyes Seven Days after Laser Treatment

To further examine the effect of treatments on the development of angiogenesis and/or fibrosis, quantitative PCR on RPE isolated from eyes treated with vehicle, anti-CD14 or high dose aflibercept was performed seven days after laser treatment. Genes examined included Vegf120, Vegf164, Vegf188, tgfb1, and Col1a1.

Figure 4:
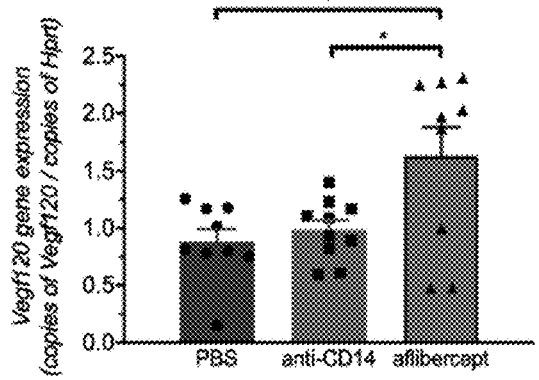
FIG. 4 is a graphical representation of VEGF isoform expression in RPE isolated from eyes treated with PBS, anti-CD14 or aflibercept (80 µg/µl) seven days after laser induced CNV. (A) Vegf120 gene expression (copies Vegf120/copies of Hprt). (B) Vegf120 gene expression (copies Vegf120/copies of Gapdh). (C) Vegf164 gene expression (copies Vegf164/copies of Hprt). (D) Vegf164 gene expression (copies Vegf164/copies of Gapdh). (E) Vegf188 gene expression (copies Vegf188/copies of Hprt). (F) Vegf188 gene expression (copies Vegf188/copies of Gapdh).
Figure 4:
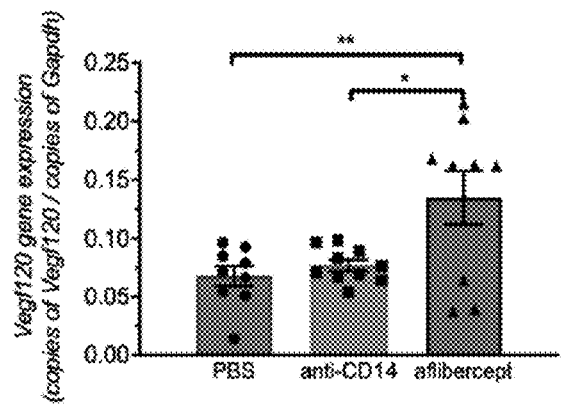
Figure 4:
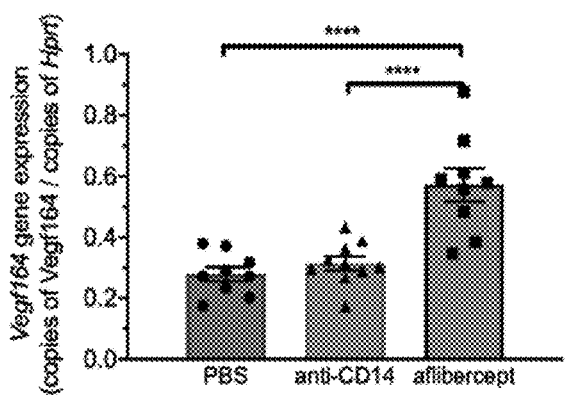
Figure 4:
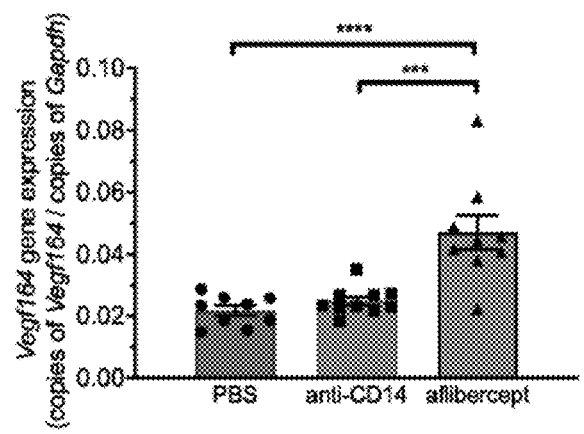
Figure 4:
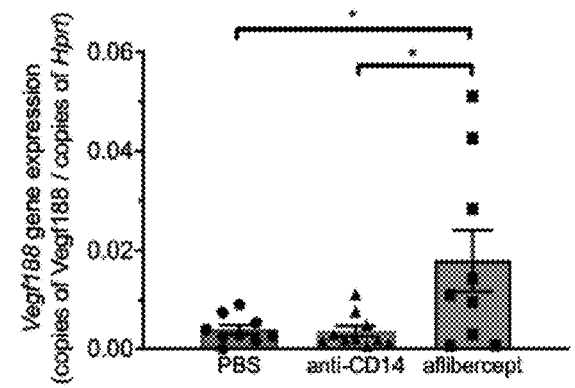
Figure 4:
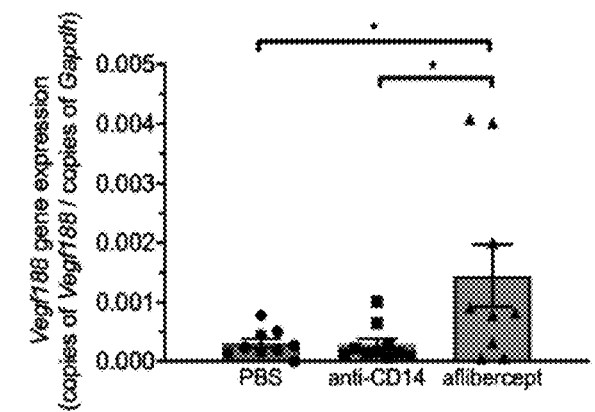
Figure 5:
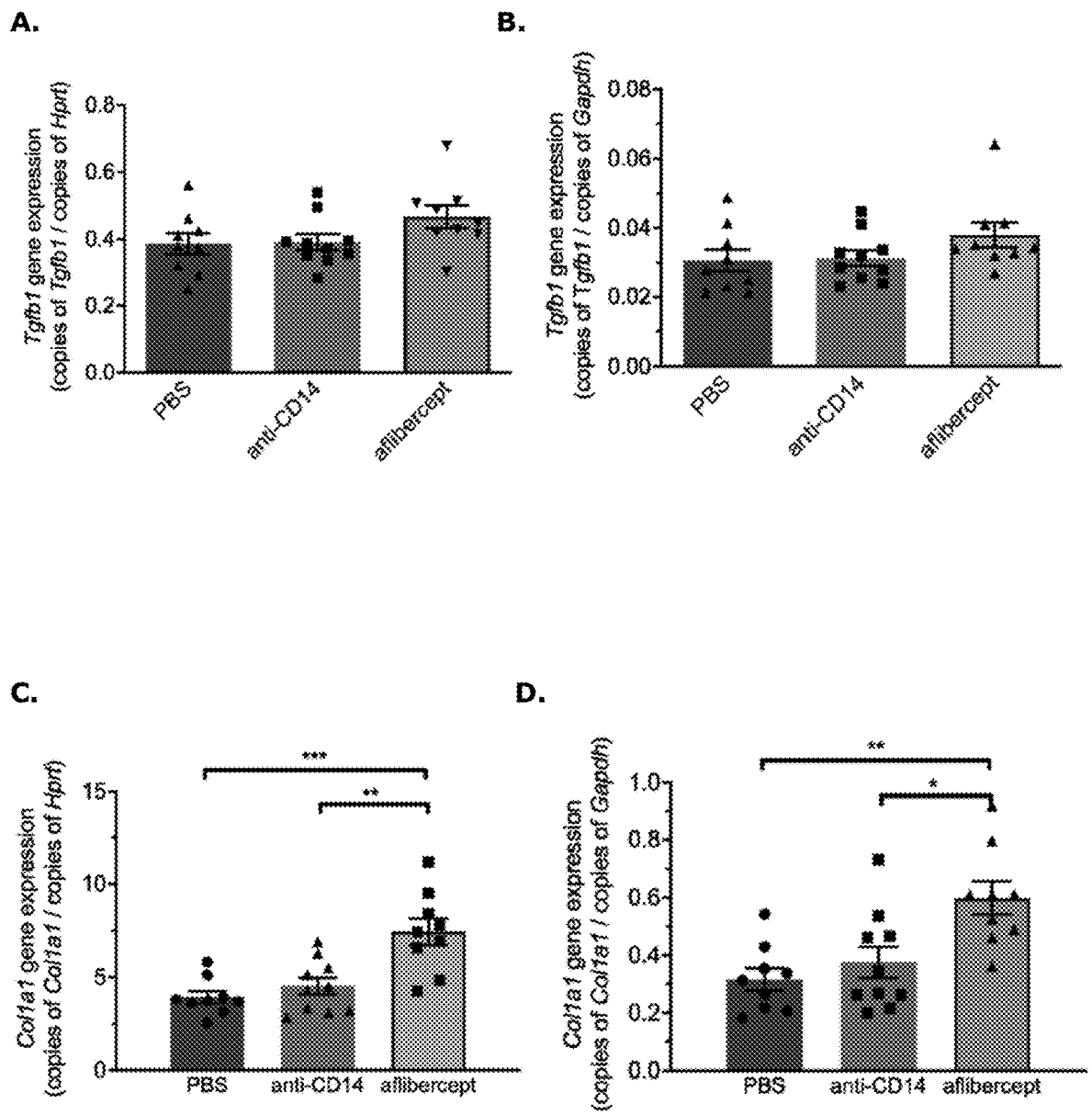
FIG. 5 is a graphical representation of Tgfb1 and Col1a1 expression in RPE isolated from eyes treated with PBS, anti-CD14 or aflibercept (80 µg/µl) seven days after laser induced CNV. (A) Tgfb1 gene expression (copies Tgfb1/copies of Hprt). (B) Tgfb1 gene expression (copies Tgfb1/copies of Gapdh). (C) Col1a1 gene expression (copies Col1a1/copies of Hprt). (D) Col1a1 gene expression (copies Col1a1/copies of Gapdh). (One way ANOVA, Posthoc Tukeys, *$p<0.05$, $p<0.01$; *$p<0.0001$).

Laser induced choroidal neovascularization did not alter the expression of housekeeping genes, Hprt and Gapdh (data not shown). Quantification of gene expression compared to either Hprt and Gapdh revealed no change in expression when comparing anti-CD14 with vehicle for any gene examined (FIGS. 4 and 5). As shown in FIG. 5, high dose aflibercept induced an increase in expression in VEGF isoforms as well as Col1a1. Tgfb1 expression was not affected by any of the treatments examined.

Analysis using a defined PCR array was used to quantify changes in expression of 84 genes known to be involved in fibrosis. It was observed that aflibercept and anti-CD14 have distinct effects on RPE gene expression. For example, aflibercept treatment increased expression of five genes that are important in the formation of extracellular matrix: Col1a2, Il4, Itga2, Mmp2 and Mmp3, something not seen with the administration of the anti-CD14 antibody.

Effect of Treatment of Expression of VEGF in RPE

Figure 6:
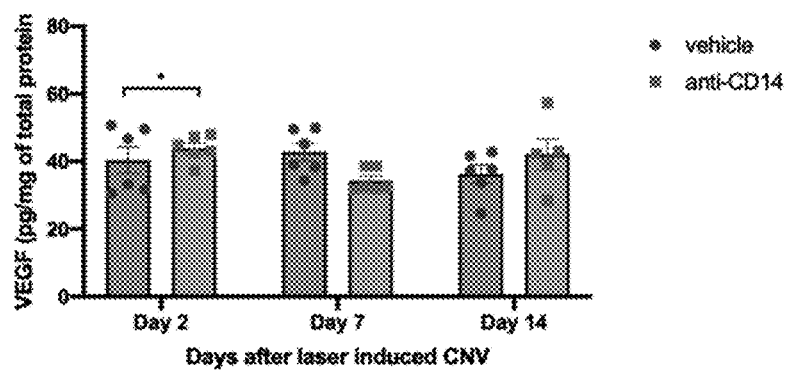
FIG. 6 is a graphical representation of VEGF expression in the retina and RPE at 2, 7 and 14 days after laser induced CNV with treatment with anti-CD14 antibody. (A) Graph of mean+SEM (and individual data) for VEGF expression in the retina. (B) Graph of mean+SEM (and individual data) for VEGF expression in the RPE. (N=6 per group; Two-way ANOVA; posthoc Tukeys test, *$p<0.01$).
Figure 6:
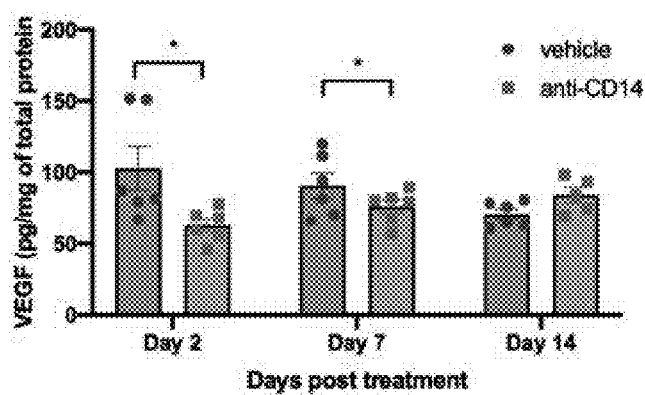

In view of the changes in fluorescein lesion size, it was next examined whether anti-CD14 reduced expression of VEGF in the RPE compared to vehicle and aflibercept. As shown in FIG. 6, VEGF protein expression was far higher in the RPE than retina. VEGF expression was reduced by anti-CD14 compared to vehicle controls 2 and 7 days after laser induced CNV in the RPE (Two-way ANOVA, day-ns; treatment-ns; interaction p=0.014; posthoc Tukeys test p=0.02). These results are consistent with the reduction in laser induced lesion size shown above in FIG. 1 and suggest that anti-CD14 has effects on VEGF expression.

Effect of Treatment on Recruitment of Innate Immune Cell Populations

An important mechanism proposed to contribute to the development of fibrosis is through the effect that influx of innate immune cells into the subretinal space has on the RPE. Flow cytometry on isolated RPE/choroid complexes was used to ascertain whether anti-CD14 and/or aflibercept influenced the recruitment of innate immune cell populations into the posterior eye.

Figure 7:
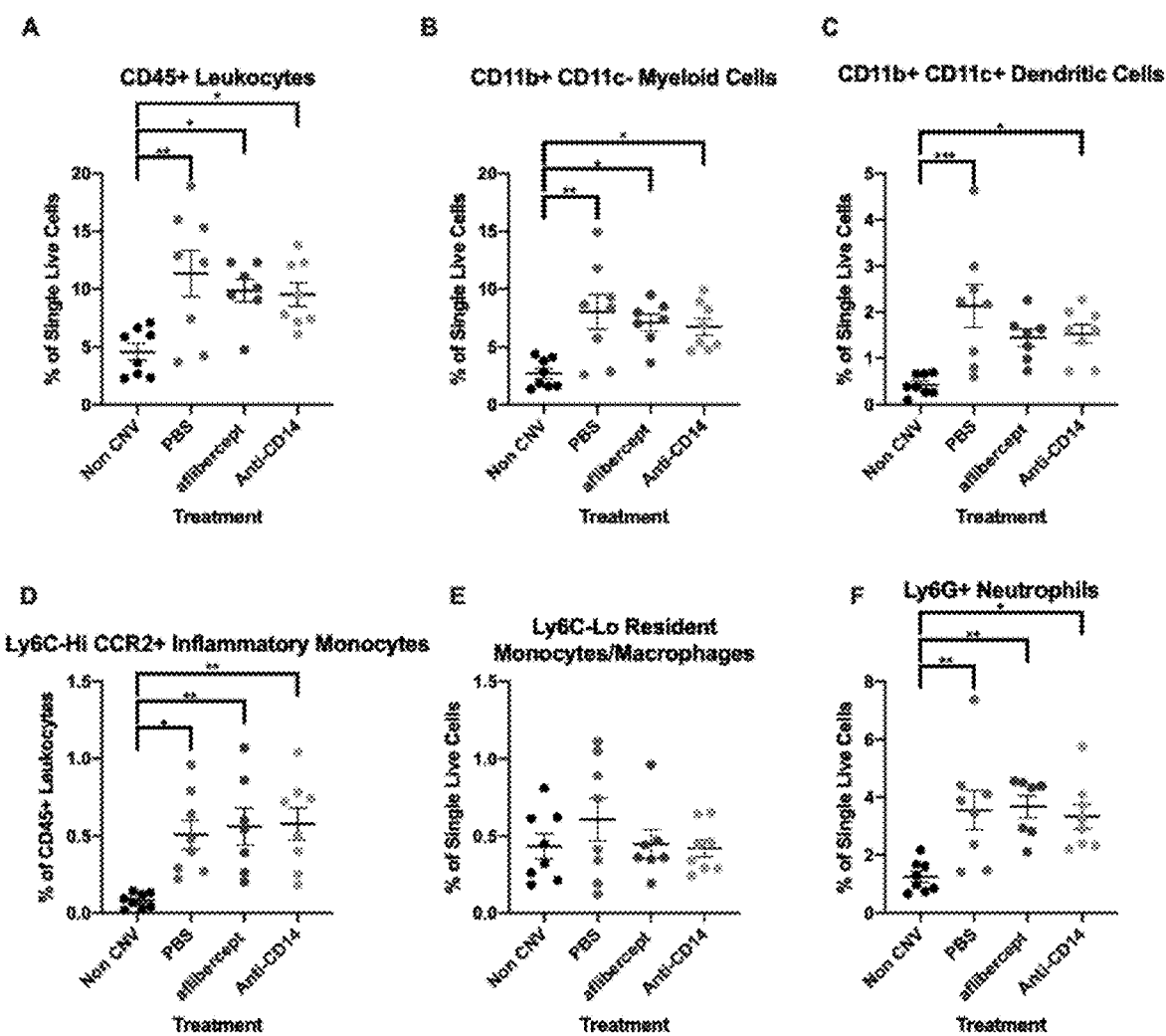
FIG. 7 is a graphical representation of the recruitment of CD45+ leukocytes population and subpopulations (A-F) across different treatments at two days post-CNV. Data are representative of four independent experiments. Each population is represented as a percentage of single live cells. N=7-8 per group, mean±SEM. One-way ANOVA, *$P<0.05$, $P<0.01$, *$P<0.001$.

FIG. 7 shows the percentage of single live cells in the RPE/choroid that are leucocytes (CD45+), myeloid cells, dendritic cells, inflammatory monocytes, resident monocytes/macrophages, and neutrophils present within RPE/choroids 2 days after laser induced CNV. Overall, there was an increase in recruitment into the posterior eye of all six cell types, and treatment with aflibercept or anti-CD14 did not alter this recruitment. It was also confirmed whether different proportions of cells that make of the broad group of leucocytes showed any changes, i.e. the change if any in the proportion of CD45+ leucocytes that is myeloid cells, dendritic cells, inflammatory monocytes, monocytes/macrophages or neutrophils. In all cell types, whilst there was an increase in the proportion within the make-up of CD45+ leucocytes, this was unaffected by treatment with either aflibercept or anti-CD14 (data not shown).

Figure 8:
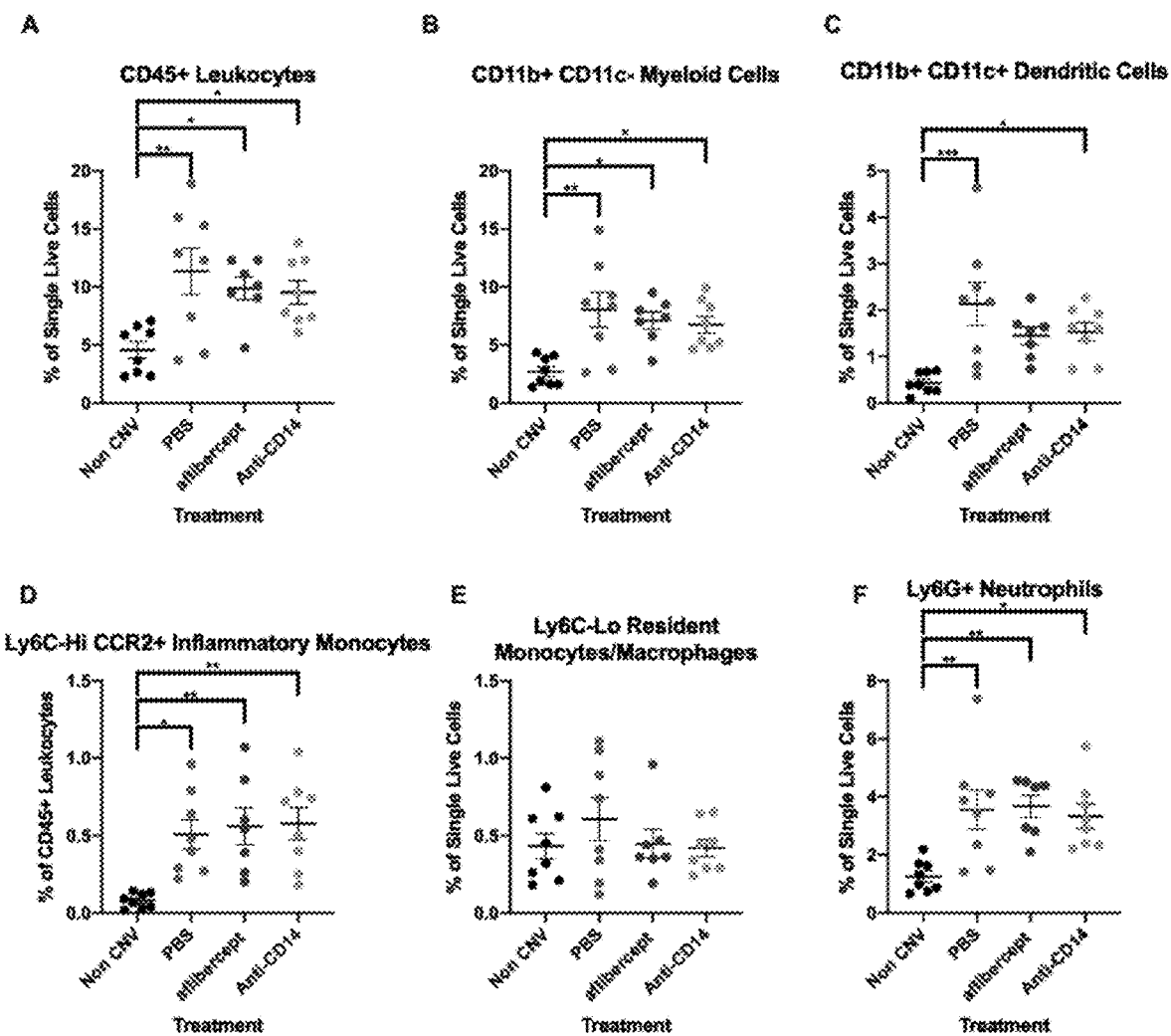
FIG. 8 is a graphical representation of the recruitment of CD45+ leukocytes population and subpopulations (A-F) across different treatments at 7 days post-CNV as assessed by flow cytometry. Data are representative of two independent experiments. N=4-8 per group, mean±SEM. One-way ANOVA, *P<0.05, P<0.01, **P<0.0001.

FIG. 8 shows the recruitment of leucocytes, and the proportion of leucocytes that is represented by myeloid cells, dendritic cells, inflammatory monocytes, resident monocytes/macrophages, and neutrophils present within RPE/choroids 7 days after laser induced CNV. The most significant trend observed at this time point was a reduction in $CD45^+/CD11b^+/Ly6G^+$ neutrophils in eyes treated with anti-CD14.

Figure 9:
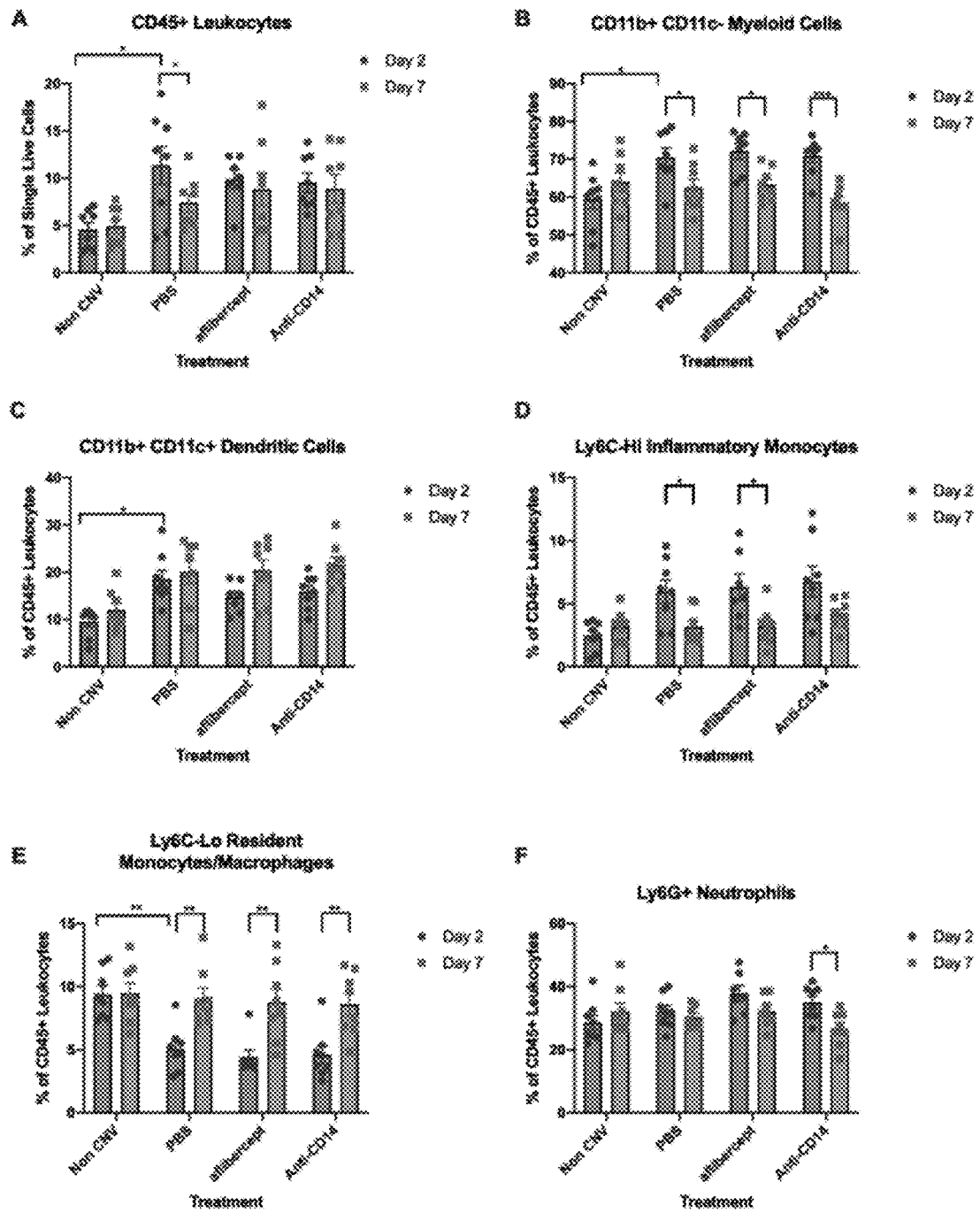
FIG. 9 is a graphical representation of the recruitment of CD45+ leukocytes population and subpopulations (A-F) post-CNV across the 7-day time course for each treatment. Data are representative of six independent experiments. N=4-8 per group, mean±SEM. Two-way ANOVA, *P<0.05, P<0.01, **P<0.0001.

A comparison in the recruitment of leucocytes and myeloid cells between 2 and 7 days is shown in FIG. 9. Importantly, leucocytes and $CD11b^+/CD11c^-$ myeloid cells show greater recruitment 2 days after laser induced CNV compared to 7 days. Moreover, anti-CD14 treatment reduced the number of neutrophils compared to vehicle controls 7 days after laser induced CNV. These findings suggest that there is an immediate influx of a range of leucocyte and cells in response to laser, although anti-CD14 may have a role in reducing neutrophil numbers after 7 days.

Figure 10:
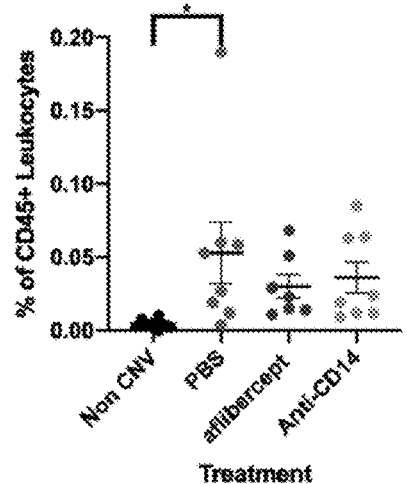
FIG. 10 is a graphical representation of the recruitment of leucocytes, and the proportion of leucocytes that is represented by myeloid cells, dendritic cells, inflammatory monocytes, resident monocytes/macrophages, and neutrophils present within RPE/choroids 7 days after laser induced CNV. (A) Changes in the recruitment of CD45+/CD34+/CCR2+/MHCII+ cells (fibrocytes) two days after laser induced CNV. (B) Change in CD45+/CD34+/CCR2+/MHCII+ cells (fibrocytes) seven days after laser induced CNV. (C) Comparison of CD45+/CD34+/CCR2+/MHCII+ cells expressed as a percentage of live cells. Data are representative of six independent experiments. N=4-8 per group, mean±SEM. Two-way ANOVA, *P<0.05, P<0.01, **P<0.0001.
Figure 10:
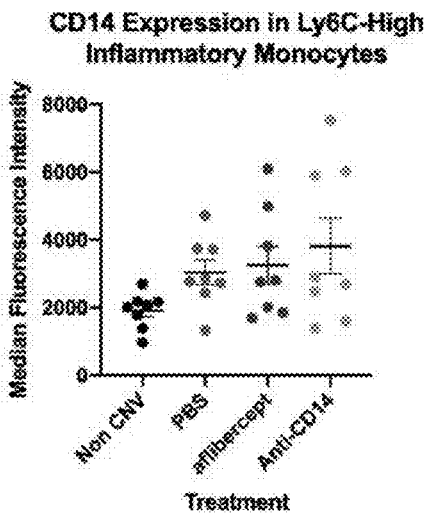
Figure 10:
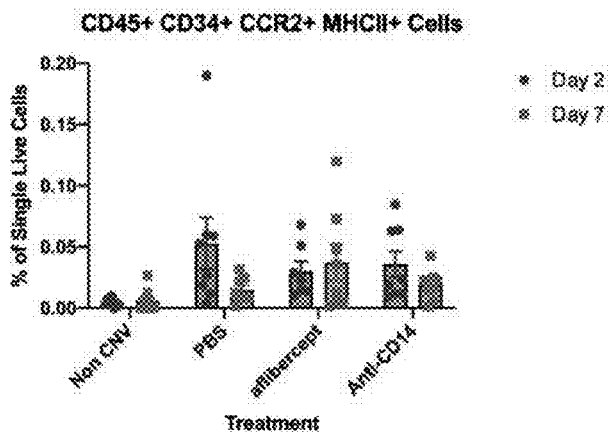

The potential role of aflibercept and anti-CD14 treatment in modifying recruitment of circulating fibrocytes ($CD45^+/CD34^+$) into the posterior eye was examined by gating for CCR2 and MHCII ($CCR2^-/MHCII^-$). Two days after laser induced CNV, there was an increase in recruitment of CD45+/CD34+ fibrocytes (FIG. 10). However, neither aflibercept nor anti-CD14 influenced recruitment of fibrocyte at this time. However, after 7 days, aflibercept showed an increase in recruitment, that was not observed in eyes treated with anti-CD14.

Figure 11:
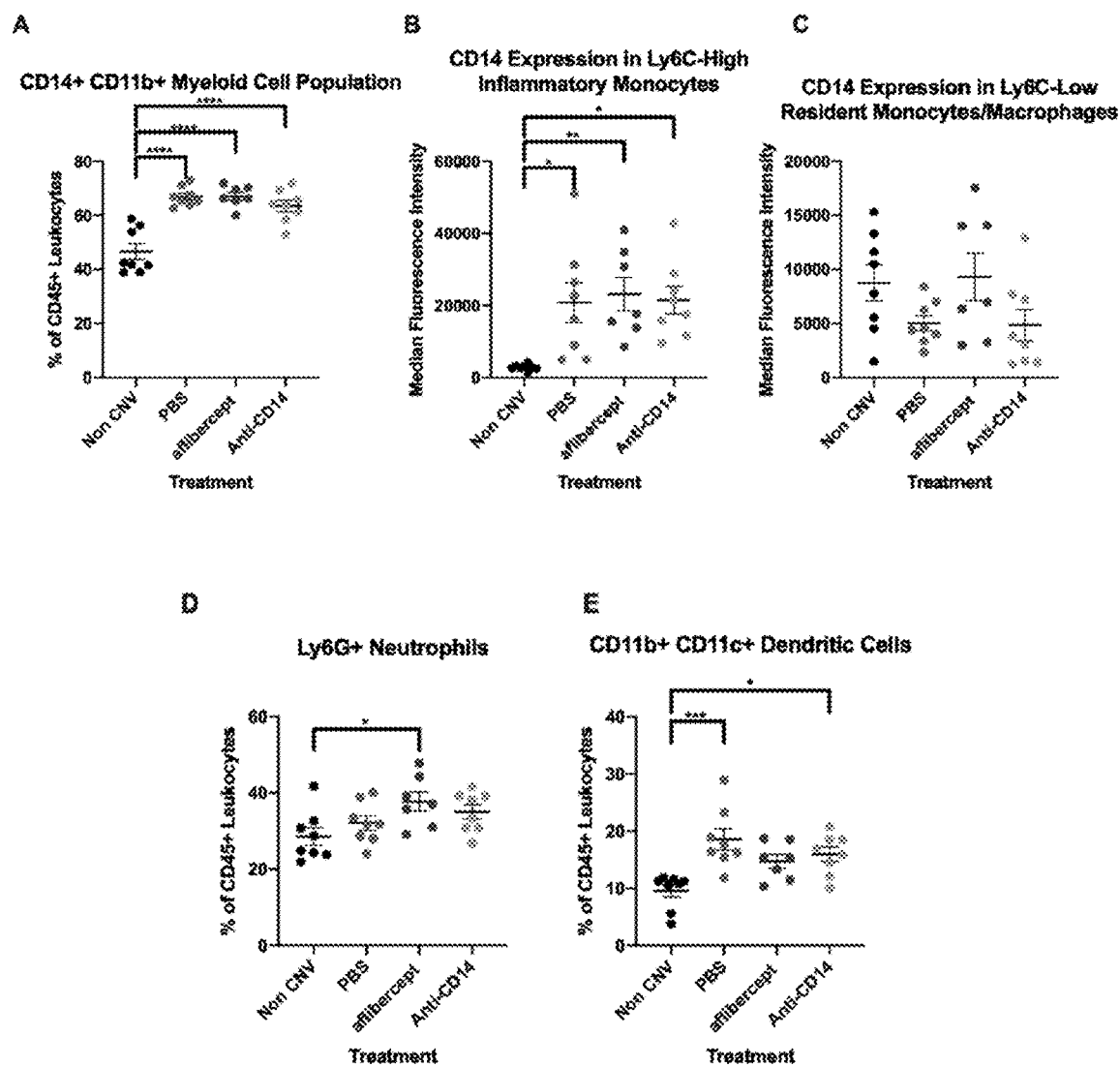
FIG. 11 is a graphical representation of the changes in the CD14+CD11b+ myeloid population and the expression of CD14 in CD11b+ myeloid cell subpopulations (A-E) across different treatments at 2 days post-CNV. Data are representative of four independent experiments. N=7-8 per group, mean±SEM. One-way ANOVA, *P<0.05, P<0.01, **P<0.0001.

The next analysis performed was to assess the expression of CD14 on the surface of myeloid cells. As shown in FIG. 11, laser induced CNV was found to increase the recruitment of CD14+ myeloid cells by two days and was also associated with an increase in surface expression of CD14 amongst inflammatory monocytes, resident monocytes/macrophages, and dendritic cells. Treatment with anti-CD14 abrogated the laser induced change in CD14 expression in dendritic cells.

Figure 12:
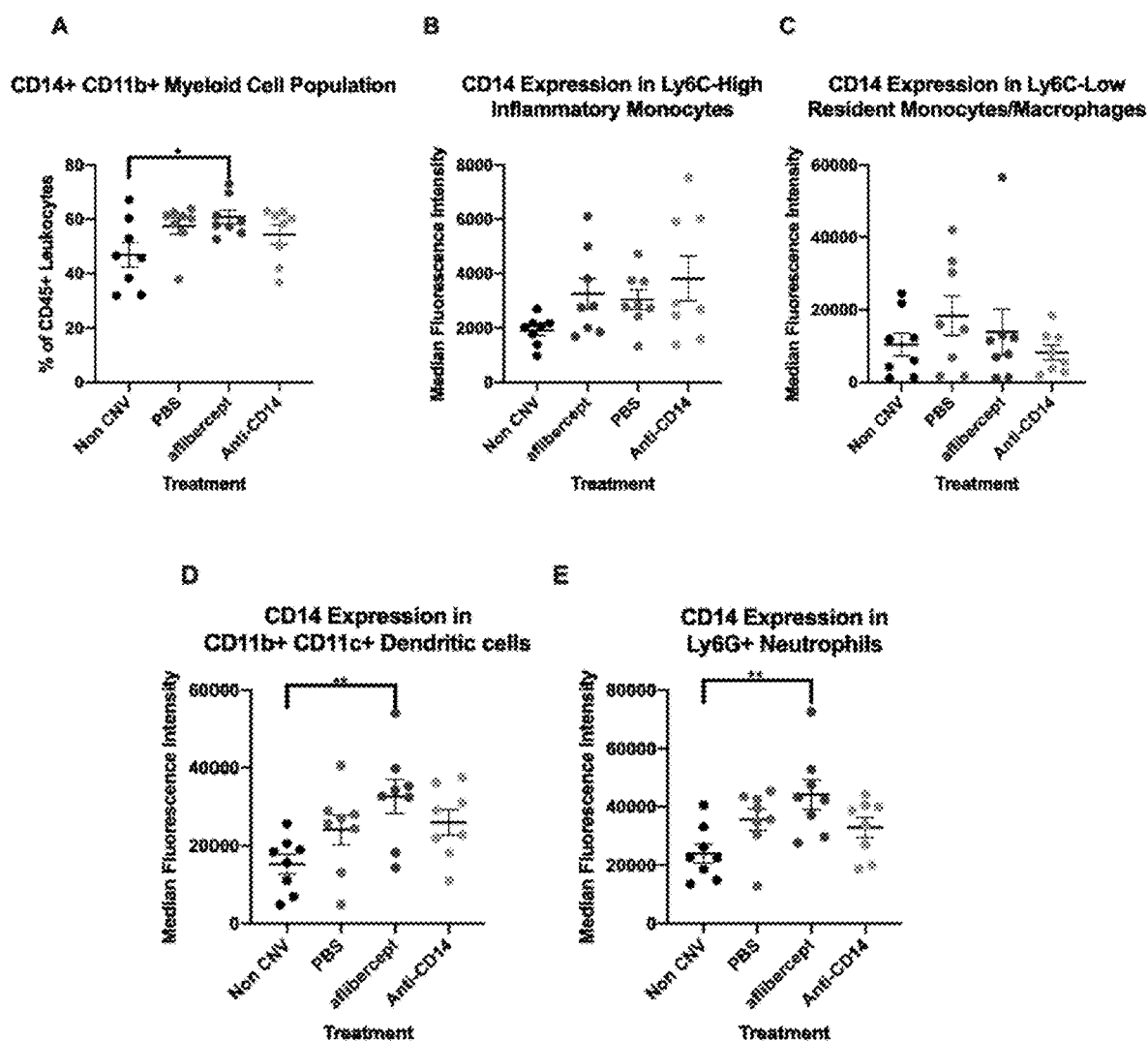
FIG. 12 is a graphical representation of CD11b+ myeloid cell subpopulations (A-E) across different treatments at 7 days post-CNV (A-E). Data are representative of two independent experiments. N=4 per group, mean±SEM. One-way ANOVA, *P<0.05, P<0.01, *P<0.001.

Laser induced effects on CD14+ recruitment and expression 7 days after laser treatment are shown in FIG. 12. There was an increase in recruitment of $CD14^+$ myeloid cells by seven days. CD14 expression was increased after laser induced CNV only in neutrophils. Treatment with aflibercept or anti-CD14 had no effect on these changes in CD14 recruitment and expression.

Figure 13:
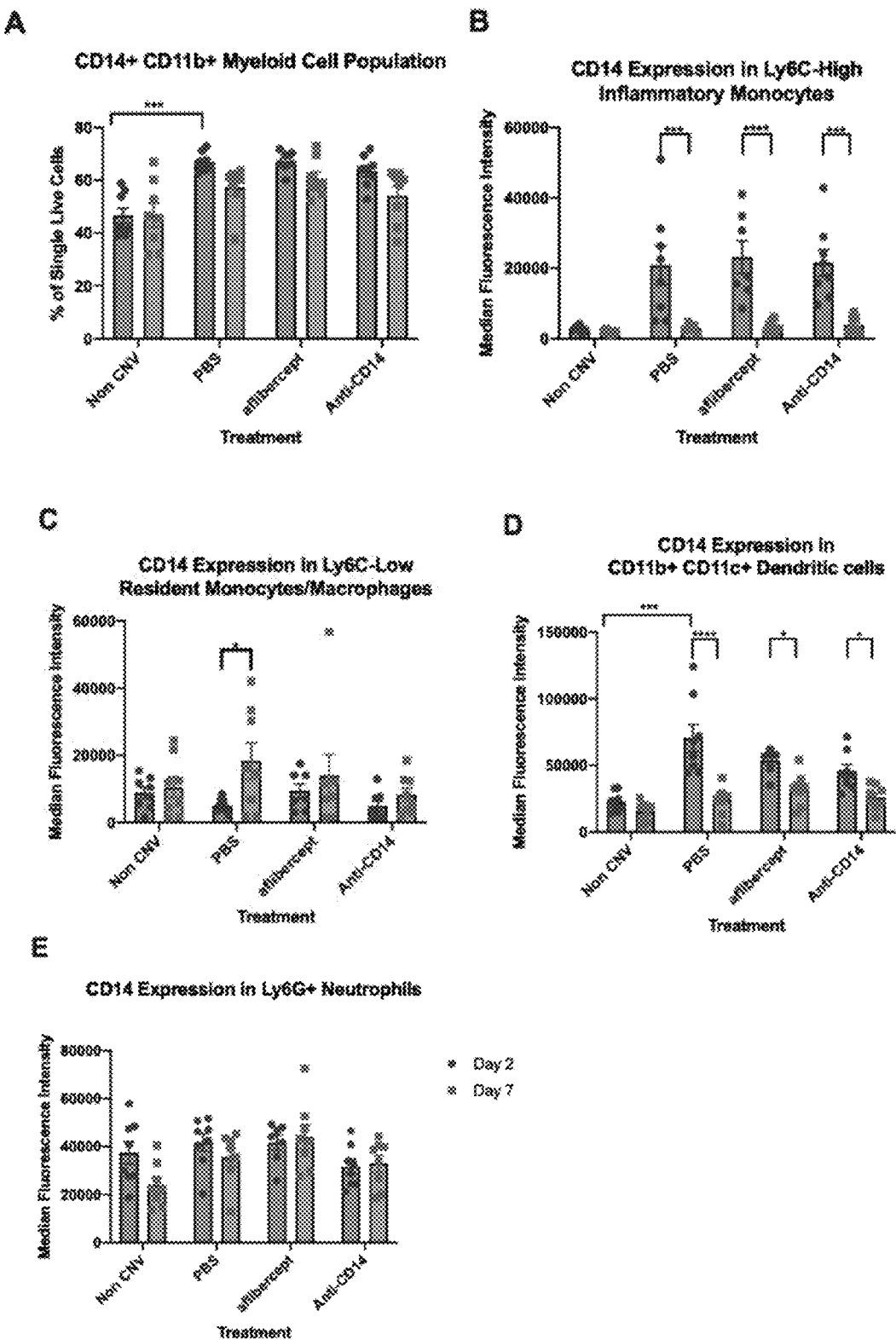
FIG. 13 is a graphical representation of changes in the CD14+CD11b+ myeloid population and the expression of CD14 in CD11b+ myeloid cell subpopulations (A-E) post-CNV across the 7-day time course for each treatment. Data are representative of six independent experiments. N=4-8 per group, mean±SEM. Two-way ANOVA, *P<0.05, P<0.01, *P<0.001.

FIG. 13 shows the laser induced effects on CD14 recruitment and expression over 2 and 7 days. Notably, an increase in CD14 expression was noted on inflammatory monocytes after 2 days, that was restored to baseline by 7 days.

However, treatment with aflibercept or anti-CD14 had no effect in influencing CD14 recruitment or expression.

C. Discussion

This study clearly demonstrates that administration of an anti-CD14 antagonist antibody reduced both laser-induced lesion size and fibrosis at 7 days, and significantly reduced the level of VEGF protein expression in the RPE between 2 and 7 days after laser-induced CNV (compared to vehicle-treated CNV). By comparison, aflibercept reduced laser-induced lesion size but not fibrosis at 7 days and this was associated with an increased gene expression of all VEGF isoforms and Col1a1 in the RPE at 7 days (although this increase in VEGF gene expression may be a compensatory mechanism to use of high dose (80 µg/µl) of aflibercept).

In order to compare the effect of anti-CD14 with standard treatment, the effect of three doses of aflibercept as well as a mouse anti-VEGF164 neutralizing antibody on fluorescein leakage and fibrosis was examined. In contrast to the dosage of aflibercept used in clinical practice for treatment of wet AMD (dosage in the eye ~ 0.45 mg/ml or 0.45 µg/µl), only a 20 fold higher dose was found to be effective in the mouse induced CNV model (the 80 µg/µl injection results in vitreal concentration of 10 µg/µl). This may be because of differences in specificity of aflibercept for mouse VEGF compared to human VEGF.

It was observed that high dose aflibercept reduced lesion size following laser treatment but did not reduce fibrosis. This is consistent with clinical results that show with long term treatment using aflibercept, fibrosis reduces vision in approximately 50% of patients with wet AMD. The studies show that in vehicle treated (and untreated) eyes, there is a correlation between fluorescein lesion size and fibrosis. When lesions fail to heal (i.e. are larger), the level of fibrosis is greater. On this basis, a treatment (e.g. aflibercept) that reduces lesion size in this mouse model might be expected to reduce fibrosis and any comparison of treatments such as between aflibercept and anti-CD14 might be expected to reduce lesion size and fibrosis simply by different extents. However, this was not the case for any concentration of aflibercept—neither aflibercept nor anti-VEGF164 reduced fibrosis to any extent. In contrast, treatment with anti-CD14 did reduce fibrosis and importantly, did this in a manner that was independent of lesion size.

In order to further study whether the anti-CD14 antibody attenuated recruitment of leucocytes especially myeloid cells into the posterior eye, the recruitment of different types of leucocytes and myeloid cells in the RPE/choroid in non-lasered control, PBS treated CNV, as well as anti-CD14 and aflibercept treated eyes, was assessed. Although recruitment of leucocytes and various myeloid cells was found to be increased within 2 days of laser induced CNV, neither anti-CD14 antibody nor aflibercept had a substantial effect in reducing recruitment of cells. The results that laser-induced CNV induced recruitment of a myeloid cells is consistent with previous studies (Tsutsumi et al. 2003, J Leukoc Biol 74(1): 25-32; Droho et al. 2019, Invest Ophthalmol Vis Sci 60(15): 5059-5069). The observation that neither aflibercept nor anti-CD14 antibody appeared to alter the broad recruitment of myeloid cells is most likely explained by the heterogeneity of cell classes evaluated. It is possible that aflibercept or anti-CD14 antibody, targets a highly specific cell type that represents only a small fraction of the cell classes examined.

To address the possibility that aflibercept or anti-CD14 antibody targets a single subtype of myeloid cells, the effect on the recruitment of CD34+CCR2+MHCII+ fibrocytes was investigated. It was observed that, like other myeloid cells, there was enhanced recruitment by two days after laser injury. There was a trend for a reduction in this cell population in anti-CD14 antibody treated posterior eyes compared to aflibercept treated eyes after 7 days.

The reduction in protein levels of VEGF in the RPE but not the retina, and in the absence of an increase in gene expression, following anti-CD14 treatment was of particular interest. The localized reduction of VEGF in the RPE rather than the retina indicated that it is likely not from infiltrating inflammatory cells (e.g. a reduction in VEGF production due to anti-CD14 attenuation of macrophage activities), as these inflammatory cells would be present in the retina rather than RPE. Rather, and quite unexpectedly, it appears that the reduction in VEGF in the RPE is the result of antagonism of the mCD14 receptors expressed on the RPE. This further indicates that the unexpected anti-fibrotic activity of the anti-CD14 antibody following laser-induced CNV is independent of, and distinct from, its anti-inflammatory and anti-angiogenic (i.e. anti-neovascularisation) activity.

In conclusion, it is clear that administration of an anti-CD14 antibody reduces both lesion size and fibrosis resulting from laser-induced CNV, and does this in a manner that is in the absence of any overt ocular toxicity. Interestingly, the reduction in fibrosis in the retina appears to be through a novel mechanism that is not related to lesion size (i.e. the degree of neovascularisation): inhibition of fibrosis following treatment with anti-CD14 was uniform and irrespective of the inhibition of lesion size, and VEGF proteins levels were reduced in the RPE but not the retina, suggesting that this was through antagonism of the mCD14 receptors expressed on the RPE rather and not anti-CD14 attenuation of infiltrating macrophage activity. Thus, it is clear that the anti-CD14 antibody acts on the posterior eye in a manner that is distinct from, and is beneficial in comparison to, aflibercept, which was found not to reduce fibrosis and indeed was observed to increase expression of genes that are important in the formation of extracellular matrix.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A method for reducing ocular fibrosis in a subject with wet age-related macular degeneration (AMD) who has ocular fibrosis, comprising administering to the eye of the subject amount of a CD14 antagonist antibody effective to reduce ocular fibrosis in the subject, wherein the CD14 antagonist antibody comprises:
   a) an antibody VL domain, or antigen binding fragment thereof, comprising L-CDR1, L-CDR2 and L-CDR3, wherein L-CDR1 comprises the sequence RASESVDSYVNSFLH [SEQ ID NO: 13], L-CDR2 comprises the sequence RASNLQS [SEQ ID NO: 14], and L-CDR3 comprises the sequence QQSNEDPYT [SEQ ID NO: 27]; and
   b) an antibody VH domain, or antigen binding fragment thereof, comprising H-CDR1, H-CDR2 and H-CDR3, wherein H-CDR1 comprises the sequence SDSAWN [SEQ ID NO: 16], H-CDR2 comprises the sequence YISYSGSTSYNPSLKS [SEQ ID NO: 17], and H-CDR3 comprises the sequence GLRFAY [SEQ ID NO: 18], and
wherein the CD14 antagonist antibody is either administered alone or in combination with an anti-VEGF agents.

2. The method of claim 1, wherein the CD14 antagonist antibody comprises:

a light chain comprising the amino acid sequence:
[SEQ ID NO: 28]
QSPASLAVSLGQRATISCRASESVDSYVNSFLHWYQQKPGQPPKLLIYRA

SNLQSGIPARFSGSGSRTDFTLTINPVEADDVATYYCQQSNEDPYTFGGG

TKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC
and a heavy chain comprising the amino acid sequence:
[SEQ ID NO: 29]
LQQSGPGLVKPSQSLSLTCTVTGYSITSDSAWNWIRQFPGNRLEWMGYIS

YSGSTSYNPSLKSRISITRDTSKNQFFLQLNSVTTEDTATYYCVRGLRFA

YWGQGTLVTVSSASTKGPSVFPLAPCSRSTSESTAALGCLVKDYFPEPVT

VSWNSGALTSGVHTFPAVLQSSGLYSLSSVVTVPSSSLGTKTYTCNVDHK

PSNTKVDKRVESKYGPPCPSCPAPEFLGGPSVFLFPPKPKDTLMISRTPE

VTCVVVDVSQEDPEVQFNWYVDGVEVHNAKTKPREEQFNSTYRVVSVLTV

LHQDWLNGKEYKCKVSNKGLPSSIEKTISKAKGQPREPQVYTLPPSQEEM

TKNQVSLTCLVKGFYPSDIAVEWESNGQPENNYKTTPPVLDSDGSFFLYS

RLTVDKSRWQEGNVFSCSVMHEALHNHYTQKSLSLSLGK;
or a light chain comprising the amino acid sequence:
[SEQ ID NO: 32]
DIVLTQSPASLAVSLGQRATISCRASESVDSYVNSFLHWYQQKPGQPPKL

LIYRASNLQSGIPARFSGSGSRTDFTLTINPVEADDVATYYCQQSNEDPY

TFGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC
and a heavy chain comprising the amino acid sequence:
[SEQ ID NO: 33]
DVQLQQSGPGLVKPSQSLSLTCTVTGYSITSDSAWNWIRQFPGNRLEWMG

YISYSGSTSYNPSLKSRISITRDTSKNQFFLQLNSVTTEDTATYYCVRGL

RFAYWGQGTLVTVSSASTKGPSVFPLAPCSRSTSESTAALGCLVKDYFPE

PVTVSWNSGALTSGVHTFPAVLQSSGLYSLSSVVTVPSSSLGTKTYTCNV

DHKPSNTKVDKRVESKYGPPCPSCPAPEFLGGPSVFLFPPKPKDTLMISR

TPEVTCVVVDVSQEDPEVQFNWYVDGVEVHNAKTKPREEQFNSTYRVVSV

LTVLHQDWLNGKEYKCKVSNKGLPSSIEKTISKAKGQPREPQVYTLPPSQ

EEMTKNQVSLTCLVKGFYPSDIAVEWESNGQPENNYKTTPPVLDSDGSFF

LYSRLTVDKSRWQEGNVFSCSVMHEALHNHYTQKSLSLSLGK.

3. The method of claim 2, wherein the CD14 antagonist antibody is IC14.

4. The method of claim 3, wherein IC14 is administered in combination with an anti-VEGF agent.

5. The method of claim 4, wherein the anti-VEGF agent is selected from the group consisting of an anti-VEGF antibody, anti-VEGF antibody mimetic, VEGF Trap molecule, soluble fms-like tyrosine kinase-1, and a tyrosine kinase inhibitor.

6. The method of claim 5, wherein the anti-VEGF antibody is selected from the group consisting of brolicizumab, ranibizumab and faricimab.

7. The method of claim 5, wherein the VEGF Trap molecule is aflibercept or conbercept.

8. The method of claim 5, wherein the VEGF antibody mimetic is abicipar pegol.

9. The method of claim 5, wherein the tyrosine kinase inhibitor is a Tie2 inhibitor or an Ang-2 inhibitor.

10. The method of claim 4, wherein the subject has received an anti-VEGF agent for at least 3, 6, 9, 12, 14, 16 or 18 months.

11. The method of claim 1, wherein the subject has received an anti-VEGF agent for at least 3, 6, 9, 12, 14, 16 or 18 months.

12. The method of claim 1, wherein the anti-VEGF agent is selected from the group consisting of an anti-VEGF antibody, anti-VEGF antibody mimetic, VEGF Trap molecule, soluble fms-like tyrosine kinase-1, or a tyrosine kinase inhibitor.

13. The method of claim 12, wherein the anti-VEGF antibody is selected from the group consisting of brolicizumab, ranibizumab and faricimab.

14. The method of claim 12, wherein the VEGF Trap molecule is aflibercept or conbercept.

15. The method of claim 12, wherein the anti-VEGF antibody mimetic is abicipar pegol.

16. The method of claim 12, wherein the tyrosine kinase inhibitor is a Tie2 inhibitor or an Ang-2 inhibitor.

* * * * *